(12) United States Patent
Aumann et al.

(10) Patent No.: US 8,496,836 B2
(45) Date of Patent: *Jul. 30, 2013

(54) METHOD AND DEVICE FOR CHROMATOGRAPHIC PURIFICATION

(75) Inventors: Lars Aumann, Zurich (CH); Massimo Morbidelli, Zurich (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 162 days.

This patent is subject to a terminal disclaimer.

(21) Appl. No.: 12/916,367

(22) Filed: Oct. 29, 2010

(65) Prior Publication Data

US 2011/0042310 A1 Feb. 24, 2011

Related U.S. Application Data

(63) Continuation of application No. 11/919,540, filed as application No. PCT/CH2006/000232 on Apr. 27, 2006, now Pat. No. 7,837,881.

(30) Foreign Application Priority Data

Apr. 29, 2005 (EP) .................................. 05405327
Jul. 1, 2005 (EP) .................................. 05405421

(51) Int. Cl.
*B01D 15/08* (2006.01)
*C02F 1/28* (2006.01)

(52) U.S. Cl.
USPC ........... 210/656; 210/659; 210/198.2; 422/70

(58) Field of Classification Search
None
See application file for complete search history.

(56) References Cited

U.S. PATENT DOCUMENTS

| 4,031,155 | A | 6/1977 | Healy et al. |
| 4,234,520 | A | 11/1980 | Priegnitz |
| 5,560,827 | A | 10/1996 | Hester et al. |
| 6,214,125 | B1 | 4/2001 | Hyoky et al. |

(Continued)

FOREIGN PATENT DOCUMENTS

| EP | 0 495 640 A1 | 7/1992 |
| WO | 02/40129 A2 | 5/2002 |
| WO | 2004/014511 | 2/2004 |
| WO | 2004/039468 A2 | 5/2004 |

OTHER PUBLICATIONS

Jura et al, "Simulated moving-bed chromatography and its application to chirotechnology", Tibtech, vol. 18, pp. 108-118, Ellsevier Science Ltd., Mar. 2000.

(Continued)

*Primary Examiner* — Katherine Zalasky
(74) *Attorney, Agent, or Firm* — Sughrue Mion, PLLC

(57) ABSTRACT

A process for continuous or quasi-continuous purification of a multi-component mixture (F) by means of individual chromatographic columns through which the mixture is fed by means of at least one solvent(s). The multi-component mixture (F) at least comprises light impurities (A), an intermediate product (B) to be purified and heavy impurities (C), and the columns are grouped into at least four sections ($\alpha,\beta,\gamma,\delta$). After or within a switch time ($t^*$) the last column from the first section ($\alpha$) is moved to the first position of the second section ($\beta$), the last column of the second section ($\beta$) is moved to the first position of the third section ($\gamma$), the last column of the third section ($\gamma$) is moved to the first position of the fourth section ($\delta$) and the last column of the fourth section ($\delta$) is moved to become the first column of the first section ($\alpha$).

18 Claims, 29 Drawing Sheets

U.S. PATENT DOCUMENTS 6,740,243 B2    5/2004   Wankat
2004/0063992 A1 4/2004   Chiang et al.
2004/0129137 A1 7/2004   Chin et al.
2004/0241878 A1 12/2004  Thommes et al.

OTHER PUBLICATIONS

Zhang et al., "PowerFeed operation of simulated moving bed units: changing flow-rates during the switching interval", Journal of Chromatography A. 1006, pp. 87-99, 2003, Elsevier B.V.

Rajendran et al, "Effect of pressure drop on solute retention and column efficiency in supercritical fluid chromatography", Journal of Chromatography A, 1092, pp. 149160, 2005, Elsevier B.V.

Gottschlich et al., "Purification of monoclonal antibodies by simulated moving-bed chromatography", Journal of Chromatography, Amsterdam NL., vol. 765, No. 2, pp. 201-206, Mar. 28, 1997.

Gottschlich et al., "Continuous biospecific affinity purification of enzymes by simulated moving-bed chromatography theoretical description and experimental results", Journal of Chromatography, Amsterdam NL., vol. 719, No. 2, pp. 267-274, Jan. 8, 1996.

Antos et al. Application of gradients in the simulated moving bed process. Chemical Engineering Science, 56 (2001) 667-6682.

METHOD AND DEVICE FOR CHROMATOGRAPHIC PURIFICATION

This is a Continuation of application Ser. No. 11/919,540 filed Oct. 26, 2007, claiming priority based on European Patent Application No. 05 405 327.7 filed Apr. 29, 2005 and European Patent Application No. 05 405 421.8 filed Jul. 1, 2005, the contents of all of which are incorporated herein by reference in their entirety.

TECHNICAL FIELD

The invention relates to the field of multicolumn purification processes and their optimizations.

BACKGROUND OF THE INVENTION

Batch chromatography is well known and routinely and preparatively applied in industrial productions. The technique is however rather costly in particular for large scale separation and purification due to high solvent consumption and expensive column material, and it requires an optimal use of the chromatographic equipment to be profitable.

For large scale separations in actual productions continuous processes are much more economic than batch processes. The advantages of a continuous process is for example high yield, less solvent consumption (recovery), less costly fractionation and analyses, better flexibility for the quantities to be purified etc.

One way to realize a continuous chromatographic process is the so called Simulated Moving Bed Process (SMB, for a review see e.g. Markus Juza, Marco Mazzotti and Massimo Morbidelli, Simulated moving-bed chromatography and its application to chirotechnology, Trends in biotechnology, Elsevier B.V., TIBTECH, March 2000, Vol. 18, p 108-118). This process can separate a mixture into two fractions by adjusting two inlet streams (feed, eluent) and two outlet streams (raffinate, extract). The SMB process is countercurrent so that a well-defined separation of the two fractions is possible at high yields. Typical examples for SMB technique in the industry are chiral separations, where two enantiomers are separated from a racemic mixture. If the selectivities are very small, usually a batch process results in rather small yields while however SMB allows to have high purity and high yields.

Various modifications of the SMB process have been proposed in order to optimise and tailor it to specific problems. So it has for example been proposed to vary the instants of individual connection and disconnection of the inlet streams and the outlet streams, i.e. inlet streams and outlet streams are not switched concomitantly as in classical SMB, but according to a specific and staged scheme (so-called Varicol-technique, see for example WO-A-2004/039468).

Another variation has been proposed by Morbidelli et al (see for example "PowerFeed operation of simulated moving bed units: changing flow-rates during the switching interval" by Ziyang Zhang, Marco Mazzotti, Massimo Morbidelli, Journal of Chromatography A, 1006 (2003) 87-99, Elsevier B.V.), in that in order to compensate the time-variation in the concentration of the output of the extract and raffinate due to the discrete switching after each cycle time the flow rate of the eluent is varied in a compensating manner coordinated to the switching interval, allowing to have even higher purity (so-called Powerfeed-technique).

A third and quasi-analogous variation has been proposed in that not the flow rate of the eluent but the concentration of the feed is varied in a compensating manner to achieve the same goal (so-called Modicon technique, see for example WO 2004/014511).

As already mentioned, in particular large scale chromatography is a laborious and expensive technique. It is only useful for the large scale separation of valuable molecules. The most valuable molecules on the market are biomolecules like for example peptides, proteins and antibodies. These molecules are usually purified via solvent gradient batch chromatography. In contrast to the term "separation", which in the context of this applications shall stand for the separation of a mixture into two fractions, "purification" means that the desired product is an intermediate between light and heavy adsorbing impurities, and that three fractions are generated. One SMB cycle can only split the feed stream into two fractions (separation), but for purifications, three fractions are required with the desired component in the intermediate fraction. Two staged or sequential SMB would be required to purify a multicomponent mixture with an intermediate desired biomolecule and heavy and light impurities however with the problem that if e.g. in a first stage SMB a first raffinate and a first extract is generated and in a second stage SMB the first extract is separated in a second raffinate (desired product) and a second extract, all undesired constituents which should have been separated in the first stage (and should have ended in the first raffinate) will certainly end up in the second raffinate which in particular for low concentrations of the desired fraction makes such processes useless.

Apart from the above, also other modifier variations were applied to the SMB scheme, such as for a few years SMB processes are operated also in so-called "solvent gradient mode" (see e.g. U.S. Pat. No. 4,031,155). The meaning of this "solvent gradient" is that the SMB contains sections, which operate on different modifier levels. This type of gradient is a "step gradient". For the purification of biomolecules however a smooth linear gradient would be desired, as routinely applied in (linear) solvent gradient batch purifications.

SUMMARY OF THE INVENTION

The objective of the present invention is therefore to provide an improved purification process, which allows to separate three fractions. The process shall be simple to set up in particular in view of large scale applications, and it shall allow a high purity and high yield. A process for continuous or quasi-continuous purification of a multi-component mixture is proposed by means of individual chromatographic columns through which the mixture is fed by means of at least one solvent. The aim of the process is not just separation of two fractions but the principal advantage is that a true multi-component mixture which at least comprises light impurities, an intermediate product to be purified and heavy impurities can be purified, i.e. an intermediate product can be isolated, and this even if this intermediate or desired product is only present in small amounts compared to the heavy and light impurities.

The present invention solves the above problem by combining the possibility of gradient batch chromatography with elements of simulated moving bed techniques, or rather countercurrent-principles, thereby allowing to benefit from the possibilities of gradient batch chromatography but also from continuous purification.

The object of the present invention is therefore a process according to claim 1, as well as a method to set up such a process and a device to carry out such a process.

In such a process for continuous or quasi-continuous purification of a multi-component mixture at least two, preferably at least three individual chromatographic columns are used, through which the mixture is fed by means of at least one solvent. As mentioned above, the multi-component mixture at least comprises light impurities, an intermediate product to be purified and heavy impurities, so the system is intended to actually isolate an intermediate fraction.

It has now surprisingly been found that it is possible to run columns in at least one batch mode step or position in which the outlet of one column is used to collect the desired intermediate product, as well as in at least one continuous or quasi-continuous mode step or position, wherein in this mode the outlet of at least one column is fluidly connected with the inlet of at least one other column. It has to be noted that the batch step may also include columns which are fluidly connected, but still one outlet is then taken for collecting the desired product.

One key element now is that it is surprisingly possible that said batch mode and said continuous or quasi-continuous mode can be either realized synchronously or sequentially, and after or within a switch time the columns can be moved in their positions in a counter direction to the general direction of flow of the solvent. This setup is particularly useful in case of a combination with gradient elution, but it does not necessarily depend on gradient elution.

The gist of the invention is, among other things, the fact that by means of a clever combination of continuous steps or functions and batch steps or functions, which may be carried out sequentially (in a staged manner) or synchronously, i.e. concomitantly, and countercurrent shifting of columns (quasi simulated moving bed), a most efficient purification of an intermediate fraction is possible due to the fact that in the batch steps or positions elution of the desired fraction or of the side fractions can be effected very efficiently, and due to the fact that the continuous steps or positions allow the recycling of fractions.

As the person skilled in the art will readily appreciate, the general concept not only applies to chromatographic columns as stated above and in the following, but equally to membrane adsorbers which take over the same function as the chromatographic columns. So while chromatographic columns are preferred in this context, if within this specification the expression chromatographic column is used this shall also include membrane adsorbers.

Furthermore, while this is clear to the person skilled in the art, it should be noted that in the context of the fractions to be separated, the designation "heavy" is intended to mean a compound which elutes slowly, i.e. has a comparably large affinity to the stationary phase, and which therefore elutes late in the process, while the designation "light" is intended to mean a compound which elutes quickly, i.e. has a comparably small affinity to the stationary phase, and which therefore elutes early in the process.

The present concept can equally be applied to classical liquid-solid systems, so to systems in which the mobile phase herein called "solvent" is liquid, as well as to supercritical systems, so to systems in which the solvent or fluid is in a supercritical state (so-called supercritical fluid chromatography, SFC).

In contrast to for example reversed phase chromatography, where the solvent strength is adjusted with an organic modifier, the adsorption properties of an SFC system can be equivalently controlled by adjusting the mobile phase density. Technical details, how the density affects the adsorption behaviour of solutes in SFC can e.g. be derived from an article by Arvind Rajendran, Oliver Kräuchi, Marco Mazzotti, Massimo Morbidelli entitled "Effect of pressure drop on solute retention and column efficiency in supercritical fluid chromatography" (Journal of Chromatography A, 1092 (2005) 149-160).

Instead of solvent concentration gradients (as will be discussed in much detail below) during a switch-time, in SFC pressure gradients are applied, so that the density of the supercritical solvent is adjusted in the proper way to achieve the separation desired. The pressure gradients can be adjusted by pressure controlled valves behind the chromatographic columns. In SFC the system can be operated in closed loop, because it is possible to recycle the solvent. After the supercritical solvent has left the device in section delta (see below), it can be easily reconditioned by changing its pressure and density. So if in the following mention is made of concentration gradients this, in case of a supercritical solvent, is meant to include a corresponding density variation.

One of the key features of the invention is the fact that according to a first preferred embodiment basically a specific topology of columns or of functions fulfilled by columns (sections) is proposed along these lines which in some sections provides optimum use of countercurrent principles and avoids the drawbacks of a fully closed simulated moving bed technique circle in that the sections are interconnected in a surprisingly simple but highly efficient way which allows effective purification using gradient techniques and not only separation of two but of three fractions. Thereby, a continuous process can be used together with gradient techniques, which latter in many difficult purification processes are the only way of purification available.

This is achieved in that the columns are grouped into at least four sections, in which a first section is provided with at least one inlet of solvent(s) and at least one outlet for purified intermediate product, such that it washes the purified intermediate product out of the system, but keeps the heavy impurities inside this section. In addition to that a second section is provided with at least one inlet for solvent(s) and at least one outlet connected to an inlet of a fourth section, such that it washes intermediate product, which is "contaminated" with heavy impurities into the fourth section through said outlet, but keeps the substantially pure heavy impurities inside the section, a third section is provided with at least one inlet of solvent(s) and an outlet for heavy impurities, such that it washes out the heavy impurities through said outlet and cleans the chromatographic column(s), and a fourth section is provided with at least one inlet to receive output of the outlet of the second section as well as at least one inlet for feeding in the multi-component mixture and at least one outlet for light impurities, such that it washes the light impurities out of the system, but keeps the intermediate product inside the section. In such a system, after or within a switch time the last column from the first section is moved to the first position of the second section, the last column of the second section is moved to the first position of the third section, the last column of the third section is moved to the first position of the fourth section and the last column of the fourth section is moved to become the first column of the first section. If the switching is carried out after the switch time, all columns are switched concomitantly at that moment. If the switching is carried out within the switch time it means that also the above-mentioned Varicol-technique can be applied. The quasi "short-circuit" between the second and the fourth section allows to "recycle" the intermediate fraction and to keep it in the region of the system in which it is possible to extract it without transferring it either the heavy or the light fraction. The functions of the sections may either be fulfilled synchronously, i.e. concomitantly and running side-by-side, or sequentially, i.e. in a time-wise staged manner. In the latter case there are preferably sequential steps with continuous or quasi-continuous elution and steps with batch elution within one switch time.

In another preferred embodiment of the present invention, such a process is combined explicitly with gradient techniques, i.e. the solvent(s) fed into at least one of the sections is substantially continuously varied in composition during the switch time.

According to another preferred embodiment, at least two, preferably at least three individual columns are present, and groupings of the sections are realized by single columns. This means that these functions are carried out sequentially and not simultaneously. Preferably the functions of individual sections are fulfilled sequentially with preferably alternating steps of continuous or quasi-continuous elution and steps with batch elution within one switch time.

Preferentially, the solvent(s) fed into all or at least the majority of the sections is substantially continuously varied in composition with increasing modifier concentration during the switch time. Along the sequence of the columns from the fourth to the first section, the modifier concentration is preferably increasing in a way such that after a move of the columns, the modifier concentrations in each column is substantially at the base concentration of modifier at the new position of the column and such that during the following switch time the modifier concentration inside each column is increased to the base concentration of the following position after a further move of the columns. This scheme applies to chromatographic methods like reversed phase and ion exchange chromatography, where the basic mechanism is that the modifier adsorbs and occupies adsorption sites on the resin. That means, in this case the higher the modifier concentration, the less strongly the (bio)molecules can adsorb. But in other systems like e.g. HIC (hydrophobic interaction chromatography) the mechanism is that at high salt concentration the solubility of the (bio)molecule in the liquid phase is small. So in this case the biomolecule does not like to stay in the liquid any more, it adsorbs on the solid. When the salt concentration (modifier) in the liquid is decreased, the (bio) molecule can again be solved in the liquid and desorbs from the solid surface. Correspondingly in the latter case, the modifier concentration is not increased but decreased but apart from that the system is operated in complete analogy to what is described above for the case of chromatographic methods like reversed phase and ion exchange chromatography.

If the system is run like that, the solid indeed experiences a continuous gradient as it travels along the system substantially against the principal solvent path. As known from batch chromatography, the mobile phase composition so in particular the modifier concentration can be varied linearly, it may however also be varied quasi-linearly i.e. in accordance with a specific desired profile (even individual for each column possible) during the switch time tailored to the purification problem. Analogously, in case of supercritical solvents, the density can be varied accordingly.

Technically, such a gradient can be implemented most easily if at each solvent inlet solvent with individual constant base concentration of modifier is provided, and if a solvent stream with periodically varying composition (i.e. e.g. modifier concentration), and/or flow-rate is provided to each inlet and mixed with the solvent with individual constant base concentration of modifier to establish the gradient along the system. Analogously, in case of supercritical solvents, the density can be varied accordingly.

According to a preferred embodiment of the process, at least one section comprises at least two columns. However, it has to be pointed out that in principle in particular the first, the second and the third section may also be combined into one column, the fractions of which are taken in a sequence of time separated steps to achieve the same or at least equivalent goal.

Basically the purification problem is separated in a main part which is fulfilled by the first section and which deals with extracting the desired product. The other sections are principally dealing with the most efficient separation of the interface between the desired product and the light and the heavy impurity, respectively. It thereby proves to be advantageous if at least some of the sections, preferably the second section, comprises at least two countercurrent, sequentially connected columns.

The fourth section is actually one of the keys to being able to purify the ternary mixture. It may therefore be structured in a more sophisticated way, and may e.g. comprise at least three columns grouped into three sub-sections, or less columns sequentially providing the function of these subsections. A first sub-section of this fourth section comprises at least one inlet for feeding in the multi-component mixture, preferably at a flow rate lower than the overall flow rate in the system, and at least one outlet either for direct removal of light impurities out of the system or into an inlet of the third sub-section. A second sub-section comprises at least one inlet for taking up output of the second section and at least one outlet connected to at least one input of the third sub-section. A third sub-section comprises at least one inlet for taking up output of the second sub-section and possibly at least one inlet for taking up output of the first sub-section, and at least one outlet. Also here, as in the main system, after (or within for asynchronous switching methods) a switch time the columns are moved (or correspondingly the functionality of the same column is changed by providing a different connectivity), namely a column from the first sub-section is moved to a first position of the second sub-section, a last column of the second sub-section is moved to a first position of the first section, a last column of the third section is moved to a first position of the third sub-section and a last column of the third sub-section is moved to become a column of the first sub-section. Again the functions of the three different sections of the fourth section can either be fulfilled synchronously or sequentially.

According to a particularly preferred embodiment of the present invention, the system comprises three columns, wherein the functions of the first, the second and the third section are realized by one single column, and wherein within one switch time this single column sequentially takes the function of the first section in that it is provided with an inlet for solvent and in that its outlet is used for taking the intermediate product out of the system, while the columns providing the function of the fourth section are connected in series and while by means of the outlet of the fourth section the light impurities are taken out of the system. Subsequently this single column takes the function of the second section in that it is provided with an inlet for solvent and in that its outlet is directly connected to the first column of the fourth section, while the columns providing the function of the fourth section are connected in series and while by means of the outlet of the fourth section the light impurities are taken out of the system. Subsequently this single column takes the function of the third section in that it is provided with an inlet for solvent and in that its outlet is used for collecting the heavy impurities, while the columns providing the function of the fourth section are connected in series, while by means of the outlet of the fourth section the light impurities are taken out of the system and while between the columns providing the function of the fourth section the multi-component mixture is fed into the fourth section.

In another but also preferred embodiment, pairs of sequential functions of the sections are combined within one column, and within one switch time steps of continuous or quasi-continuous elution and steps with batch elution, fulfilling those functions in sequential manner, are alternating.

In this case, preferably the fourth section comprises three sub-sections as discussed above, and in the full system three columns are provided, these three columns being connected sequentially in a step of continuous or quasi-continuous elution within a first part of one switch time, and being driven in a batch step for taking out individual fractions of the multi-component mixture within a second part of the switch time.

The fourth section may also comprise three sub-sections and in the full system four columns may be provided, these four columns being connected sequentially in a step of continuous or quasi-continuous elution within a first fraction of one switch time, and being driven in a batch step for taking out individual fractions of the multi-component mixture within a second fraction of the switch time, wherein in this batch step one of the columns has a flow rate close to or equal to zero.

According to another preferred embodiment with an even more reduced number of required columns, the system is comprised of only two columns, wherein the fourth section comprises three sub-sections. In this case, the two columns are in a first part of the switch time connected in series for continuous elution while by means of the outlet light impurities are removed from the system, in a second part of the switch time the columns are driven in batch mode for taking out the intermediate fraction on the upstream column and light impurities on the downstream column while at the same time feeding the multi-component mixture into the downstream column, in a third part of the switch time the columns are connected in series for continuous elution while by means of the outlet light impurities are removed from the system, and in a fourth part of the switch time the columns are driven in batch mode for taking out the heavy impurities on the upstream column and light impurities on the downstream column, wherein after each switch time the positions of the two columns are interchanged.

Preferentially, in a structure of the fourth system with three sub-sections, the first sub-section comprises at least two parallel columns, and/or the second and/or the third sub-section comprises at least two countercurrent parallel or sequential columns.

Preferentially, the feed is introduced into the system in a continuous manner, even more preferentially it is however introduced using a periodically pulsed concentration profile (periodic with the frequency of the switching) or with a shaped concentration profile within one switch time. Alternatively or in addition to that the flows of solvents/densities are varied within one switch time and/or the switching of individual inlets/outlets is staged within one switch time. It is particularly useful, if the flow rate in individual columns is different.

The more complicated the set up for a purification, the more important it becomes to find an easy way of setting up the parameters for such a purification scheme. In the present case this is possible by first running a standard gradient batch chromatogram of the feed and by a simple, straightforward and intuitive analysis of the batch data.

In the present situation, the setup of the parameters is possible in that in a first step a gradient batch chromatogram is run, in a second step the obtained chromatogram is divided into a first part with the light fraction, a second part with the desired fraction, a third part with the desired fraction overlapping with the heavy fraction, and a fourth part with the heavy fraction only. In a third step of the set up, the parameters of the process are then chosen such that the first section fulfils a task equal to the gradient batch chromatogram in the time of the second part, that the second section fulfils a task equal to the gradient batch chromatogram in the time of the third part, that the third section fulfils the task equal to the gradient batch chromatogram in the time of the fourth part, and that the fourth section fulfils the task equal to the gradient batch chromatogram in the time of the first part.

The optimal switch time with respect to productivity is thus preferably calculated as the time until the light impurities have been completely eluted in the gradient batch chromatogram multiplied with the flow rate of the gradient batch chromatogram divided by the maximum flow rate of the setup and divided by the number of columns which run the batch gradient until the light impurities have been completely eluted in the batch chromatogram. The flow rate in each column is preferentially determined based on the time the corresponding part takes in the gradient batch chromatogram multiplied with the batch flow rate divided by the switch time.

The present invention in addition to that relates to a device for carrying out a process as given above. In this device, a topology of at least two, preferably at least three individual chromatographic columns, but also 4, 5 or 6 columns is preferred, is provided, through which a mixture can be fed by means of at least one solvent, wherein the multi-component mixture again at least comprises light impurities, an intermediate product to be purified and heavy impurities. The device comprises means in the form of pumps, valves, connecting tubes between columns, collecting outlets, solvent inlets and at least one feed inlet which elements allow to run the columns such that in at least one batch mode step or position the outlet of one column is used to collect the intermediate product, as well as in at least continuous or quasi-continuous mode step or position the outlet of at least one column is fluidly connected with the inlet of at least one other column, wherein said batch mode and said continuous or quasi-continuous mode can either be realized synchronously or sequentially, and wherein after or within a switch time the columns are moved in their positions in a counter direction to the general direction of flow of the solvent.

Preferably and according to a first embodiment of the device, the device is structured such that columns are grouped into at least four sections, in which the first section is provided with at least one inlet of solvent(s) and at least one outlet for purified intermediate product, such that it washes the purified intermediate product out of the system, but keeps the heavy impurities inside the section, the second section is provided with at least one inlet of solvent(s) and at least one outlet connected to an inlet of the fourth section, such that it washes the intermediate product, which is contaminated with heavy impurities into the fourth section through said outlet, but keeps the pure heavy impurities inside the section, the third section is provided with at least one inlet of solvent(s) and an outlet for heavy impurities, such that it washes out the heavy impurities through said outlet and cleans the chromatographic column(s), the fourth section is provided with at least one inlet to receive output of the outlet of the second section as well as at least one inlet for feeding in the multi-component mixture and at least one outlet for light impurities, such that it washes the light impurities out of the system, but keeps the intermediate product inside the section, wherein connecting and disconnecting means are provided, allowing to move the last column from the first section to the first position of the second section after or within a switch time, to move the last column of the second section to the first position of the third section, the last column of the third section to the first position of the fourth section and the last column of the fourth section to become the first column of the first section.

Further embodiments of the present invention are outlined in the dependent claims.

SHORT DESCRIPTION OF THE FIGURES

In the accompanying drawings preferred embodiments of the invention are shown in which.

DETAILED DESCRIPTION OF THE PREFERRED EMBODIMENTS

For preparative and also analytic solvent gradient batch elutions most often linear solvent gradients with respect to time are used. For biomolecules with rectangular isotherms a linear gradient elution is often the only useful kind of elution. The system introduced in this work uses quasi-linear gradients, which are analogue to the one used in batch systems.

The linear solvent gradient of the batch elution can be split into constant levels and periodic superimposed linear gradients with a period of one switch time "t*".

This "gradient split" is explained in the following example illustrated in FIG. 1, which shows a 6 column "Linear Solvent Gradient Simulated Moving Bed (SMB)".

After a switch the modifier concentrations in the columns are at the base-step concentration as (after switch), which is indicated by the bottom line. During the next switch time the concentration inside each column is changed linearly (also nonlinearly is of course possible) up to the next level, which is indicated by the top level concentration, designated bs (before switch) in FIG. 1. When the system starts to switch at "t*", i.e. the columns are moved in a direction opposite to the flow of the solvent, the starting concentration of the new position is exactly the end concentration of the former position. Switch means in the present case, that column 6 switches to column 5, 5→4, 4→3, 3→2, 2→1, 1→6, since the solvent or eluent flows from the left to the right.

The solute molecules, inside the columns do not "see" the column switch at t*. They "notice" only the quasi continuous change of the modifier concentration as time goes by, which is the periodic part (starting from a constant level, which is different for every column, levels indicated with as in FIG. 1). Finally they can travel with the solid phase from for example column 6 backwards to column 1 and they only "feel" a linearly increasing modifier concentration from $C_{start}$ to $C_{end}$—fully analogue to a linear solvent gradient batch elution.

Figure 2:
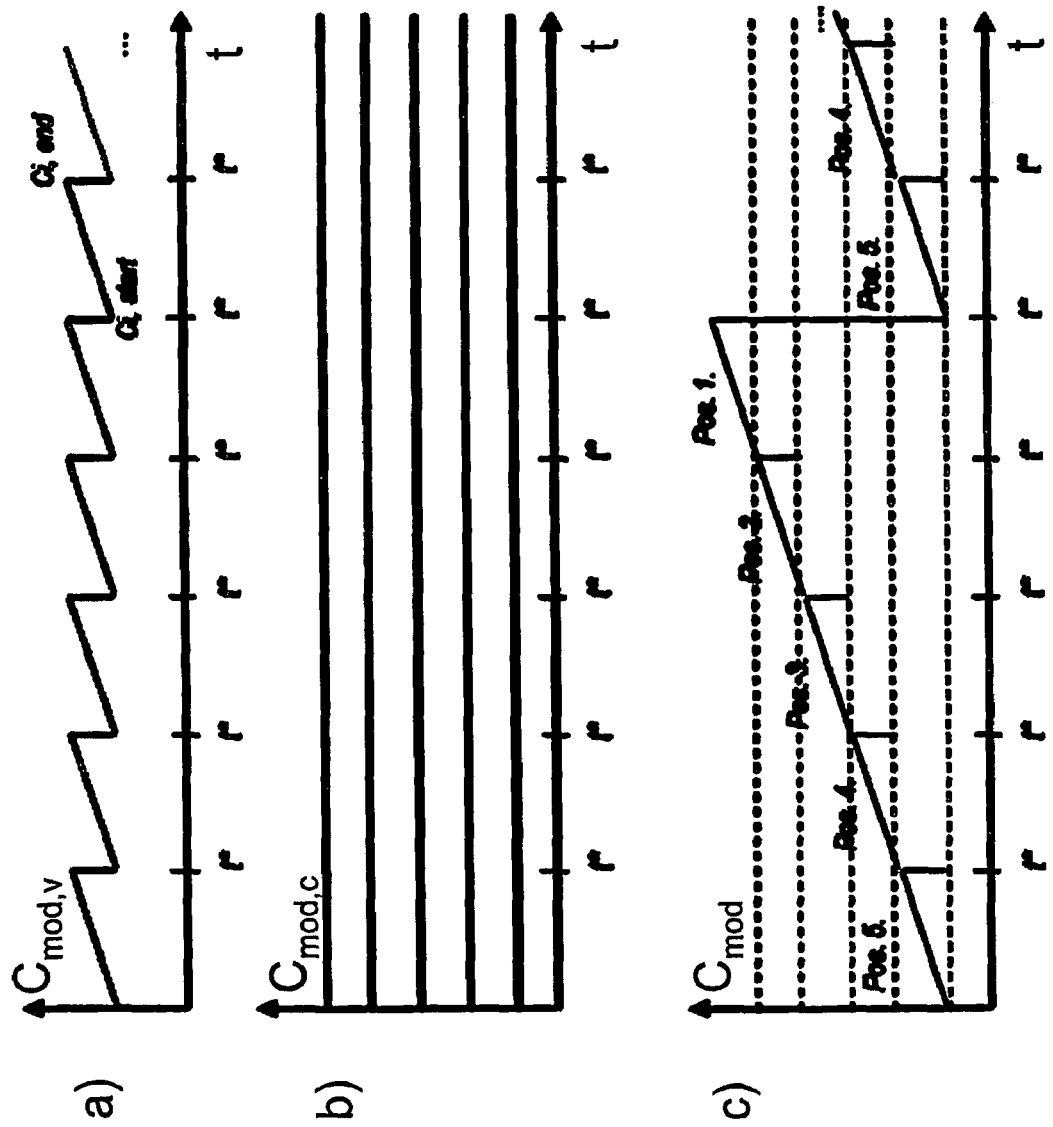
FIG. 2 shows the technical realization, here for 5 columns, of a quasi linear gradient by superimposition of a step gradient (b) plus a periodic solvent gradient (a)

FIG. 2 shows how the quasi linear gradient is effectively made available. A modifier concentration $C_{mod,v}$ (e.g. a strong solvent like acetonitrile, ACNL, added to a weak solvent like water with acid, but also salts and other modifiers are possible) which is changing as a function of time (FIG. 2 a) is combined or superimposed/mixed with constant levels of modifier concentration $C_{mod,c}$ for every column (FIG. 2b). If both concentrations are combined to $C_{mod}$, the effective gradient becomes a linear gradient from the point of view of a column. In the FIG. 2c) the modifier concentration $C_{mod}$ is plotted from the point of view of a column in a 5 column system.

When the column is at position 5. it "sees" the lowest modifier concentration. That concentration linearly increases with time. At the switch time t* the column is switched to position 4. Here again a linear concentration increase takes place, but that one starts from the concentration, which is equal to the one just before the switch in position 5. The same happens, when the column switches to positions 3. 2. and 1. After a cycle the column is switched back to position 5. where the same procedure starts again.

Figure 3:
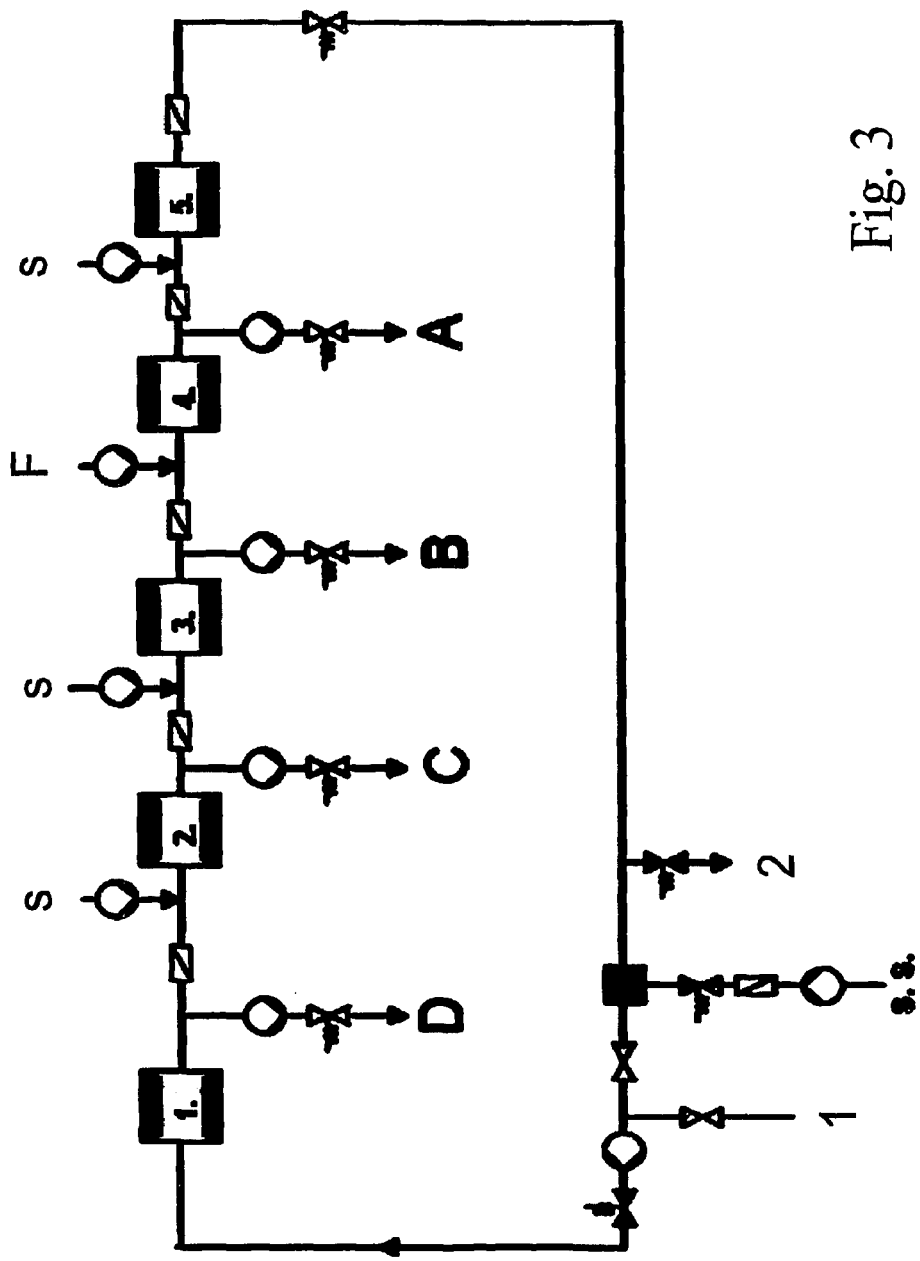
FIG. 3 shows a schematic flow sheet of a 5 column solvent gradient SMB to separate a 4 component mixture.

For "easy separations" (baseline separations), in which the selectivity of the solutes is large, a system as shown in FIG. 3. can be used. Here every column i contains an elution profile at the inlet, which contains the component washed out in the next column (i−1). the highest modifier concentration is applied to column 1. (s.s.: strong solvent) and the concentration goes down along the sequence of the columns 2.-5. (w.s.: weak solvent). In this case four fractions are separated, namely a light fraction A, two intermediate fractions B and C and one heavy fraction D.

Every column has 3 tasks (here for column no. 3): 1.) "elute one component (here component B)", 2.) "keep the others not moving (C,D)" and 3.) "catch the component, which is eluted in the next column "3−1=2"(here C)".

For easy separations (high selectivity, baseline separation), step gradients are sufficient, quasi linear gradients are actually not required nor do they substantially influence yield and selectivity of the process.

Easy separations are however rare. Normally a mixture to be purified consists of hundreds of different components of which some can have a very similar adsorption behaviour and from which actually only one or a very small number is the desired fraction. In addition to that, this desired fraction is very often very small and overshadowed by huge amounts of heavy and light components which one would like to get rid of. The SMB, which is shown in FIG. 1 would in such a situation not be able to purify the intermediate fraction of a "normal" multi-component mixture like for example a polypeptide on a reversed phase resin.

One of the problems of such a setup is therefore the fact that it is only efficiently applicable to situations in which baseline separation is present, in all other cases it will be, in particular if the desired fraction (e.g. B) is only a small percentage of the undesired fractions, very difficult if not impossible to obtain high yields and good separation. This, since any compound overlapping with the desired fraction will either be lost in a downstream or an upstream fraction and mixing of fractions in undesired orders will be unavoidable.

So if switching of the columns takes place "late", i.e. if there is no more overlap with the light fraction (e.g. A), there is not much time left to elute the desired fraction (B) and a major part of the desired fraction (B) will then be lost in the subsequent heavy fraction since it will completely and most certainly end in the outlet for fraction C. Or the desired fraction (B) will be contaminated by amounts of the light fraction (A), if the columns are switched "early" and if a partial overlap of the desired fraction B with a light fraction A in the moment of switching is put up with. It has to be pointed out that this is an inherent problem which can not be overcome by staged or sequential SMB according to FIG. 3.

To overcome these and other problems, the method according to the appended claims has therefore been developed, which is termed "Short Circuit Moving Column Technique".

One of the basic ideas behind this surprisingly efficient and simple concept is that it is possible, by means of "short-circuiting" a process similar to the one as given in FIG. 3, to get back the desired fraction in spite of the fact that switching of the columns is allowed to take place "late", i.e. if before switching of the columns the specific column 3. does almost not comprise any light fraction A any more. This is achieved basically in that overlap with the subsequent heavy fraction (in the case of FIG. 3 fraction C) is avoided, and in that by means of short-circuiting of the "solvent path", i.e. by directly connecting the output of column 2. with the inlet of column 4. any amount of desired fraction B which in a setup according to FIG. 3 would end up mixed with C and would be taken out of the system, is led back to column 4. and will then due to the counter-current switching of the columns be brought into position 3. again for elution.

Figure 1:
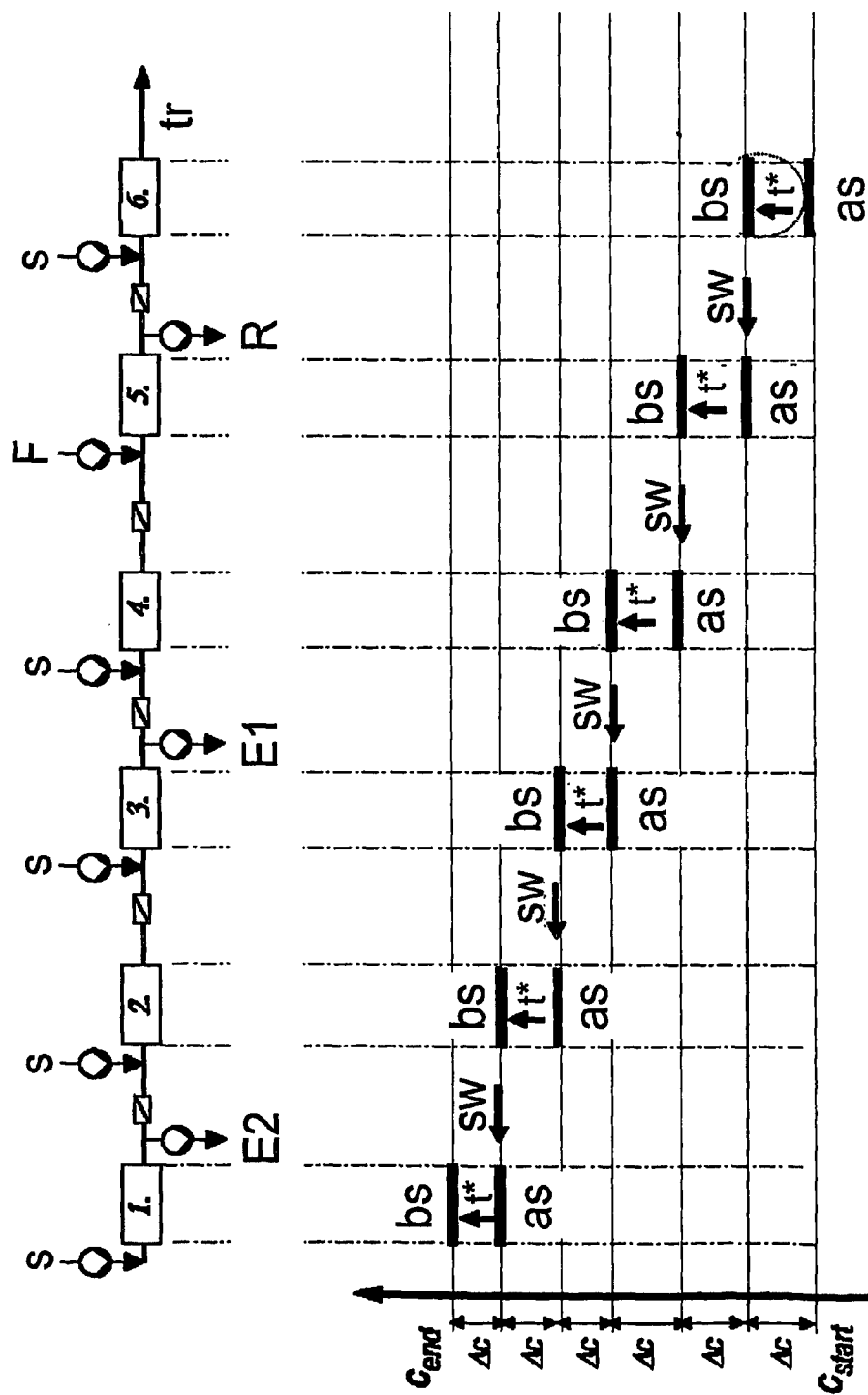
FIG. 1 shows an example of a 6 column linear solvent gradient SMB.

How to generate a quasi continuous linear solvent gradients has been introduced in FIG. 1. Feeding in solvent gradient batch elutions is done discontinuously before the elution starts. The feed is loaded at small modifier concentrations, where the adsorption of the solutes is very strong and the adsorption sites are free. After loading, the modifier concentration is increased in time and the solutes start to elute one after the other. Continuous loading in the gradient SMB shown in FIG. 1 is not very useful. The feed would have to be pulsed at the beginning of the switch, so that the gradient can perform its effect in time.

To get a high yield, column 5. in FIG. 1 needs to be switched to position 4. before the intermediate E1 breaks through. Just before the switch, column 5. still contains some light impurities (raffinate, R), which will be carried during the next switch with the liquid stream from column 4. into column 5. The negative effect is that light components will move upwards with the solid and reach a position in column 4. behind the new feed pulse. It will therefore be impossible to reach a high purity of the intermediate desired component E1.

Once the intermediate component E1 is clean at the column outlet of column 3. only a part of the purified stream is sent out of the SMB in the "Extract 1" E1 stream. The largest part flows into column 4. due to the liquid connection between column 3. and column 4. At the inlet of column 4. the heavy components are adsorbed on the resin, so that the purified intermediate E1 component is mixed with the heavy impurities E2. Then the separation becomes impossible.

Figure 4:
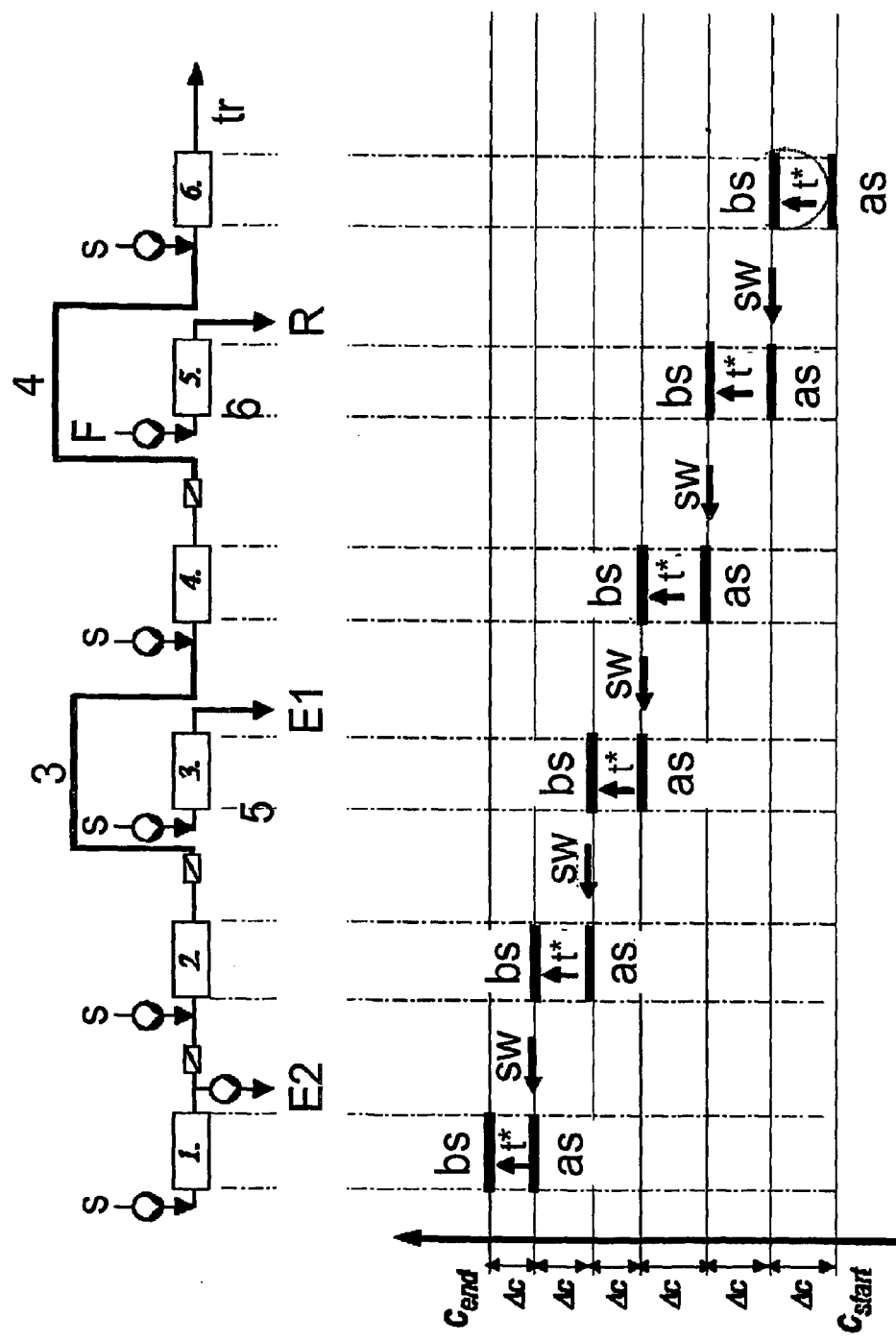
FIG. 4 shows a concrete example of a "short circuited linear solvent gradient SMB" setup.

Short Circuit Moving Column Technique solves these problems as indicated in FIG. 4. Column 3. gets no liquid connection to the other columns, column 2. is connected with column 4. and column 5. becomes available for continuous feeding, where column 4. is connected with column 6.

Figure 5:
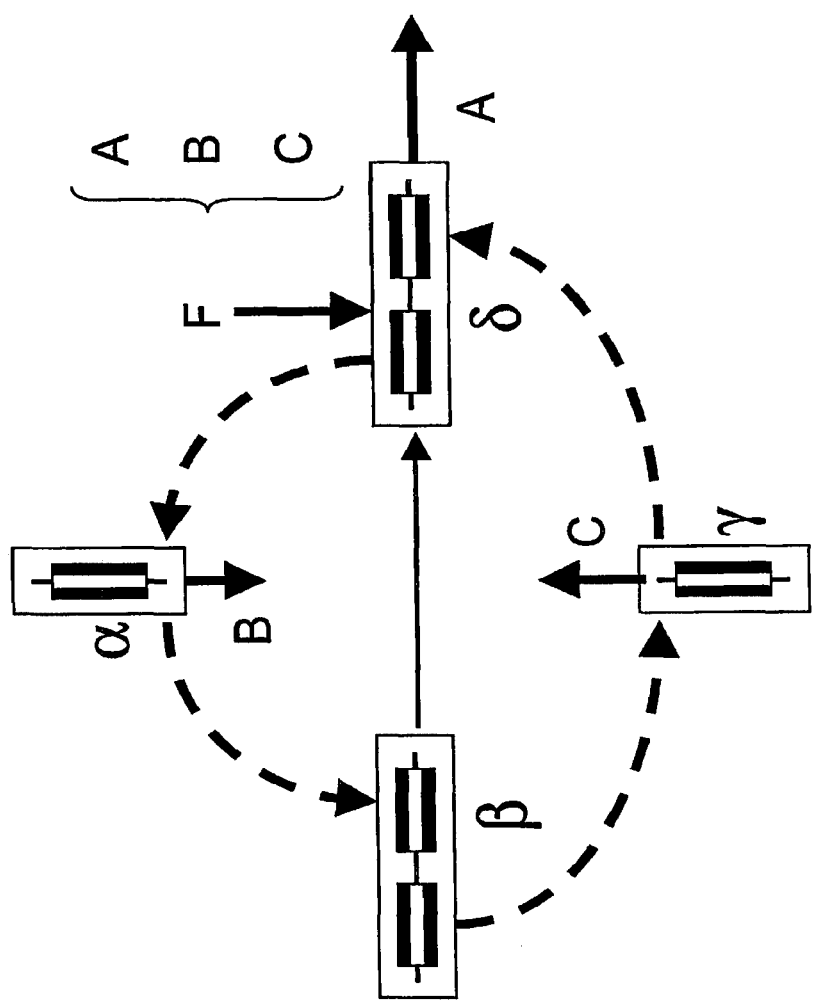
FIG. 5 shows a generalized flow sheet of the "Continuous Gradient Purification Process"

A more general approach of this technique is shown in FIG. 5, where the topology of connections of columns of FIG. 4 is generalized show the underlying principle. In this case a (constant or periodically pulsed/distributed) feed F comprising three fractions A (light fraction), B (desired fraction) and C (heavy fraction) is introduced into the system. Dashed arrows show the solid movement, i.e. the movement of the columns in the system. The horizontal arrow pointing to the right in the centre indicates the liquid recycle between the sections $\beta$ and $\delta$.

In the generalized process shown in FIG. 5, four sections $\alpha,\beta,\gamma,\delta$, which consist of one or several chromatographic columns are connected with a simulated solid movement in a closed loop (dashed arrows). After a certain time, the switch time $t^*$, the last column from section $\alpha$ is moved to the first position of section $\beta$ and the last column of section $\beta$ is moved to the first position of section $\gamma$. The last column of section $\gamma$ is switched to the first position of section $\delta$ and the last column of section $\delta$ becomes the first column of section $\alpha$. This is done in a way so that a separation between light impurities A, the desired intermediate product B and the heavy impurities C is obtained continuously. In relation to the liquid streams the movement of columns between the sections is done in cross flow, except the connection between section $\beta$-$\delta$, but inside the sections the columns can be moved countercurrently with respect to the liquid streams.

The number of columns inside the sections depends on the difficulty of the separation. If the components can be easily purified in a batch column, the system does not require countercurrent movement inside and between the sections, then every section could consist of only one column and section $\beta$ is not even required. For difficult separations however, where only partial purification can be obtained in a batch elution, one or more columns inside section $\beta$ and $\delta$ are preferred to get high yields and purities. Section $\beta$ and $\delta$ is interconnected with a liquid recycle stream (horizontal central arrow). All inlet and outlet streams are continuous, except the feed, which can be a continuous stream or a pulse. The flow rates in the individual sections and in columns within sections is not necessarily identical. The process can transfer isocratic and also linear gradient elutions into a continuous, partly countercurrent separation.

The sections have specific tasks, which are:

Section α: wash the purified intermediate product out of the system, but keep the heavy impurities inside the section.

Section β: wash intermediate product, which is contaminated with heavy impurities into section δ, but keep the pure heavy impurities inside the section.

Section γ: wash out the heavy impurities and clean the chromatographic column(s) of the section. Cleaning in place (CIP).

Section δ: wash the light impurities out of the system, but keep the desired product inside the section. Get the feed into the purification system.

Each of the sections may have a design which is tailored to the specific separation problem which has to be solved. In the subsequent FIGS. 6-8 possible variations for some of the sections are given.

Figure 6:
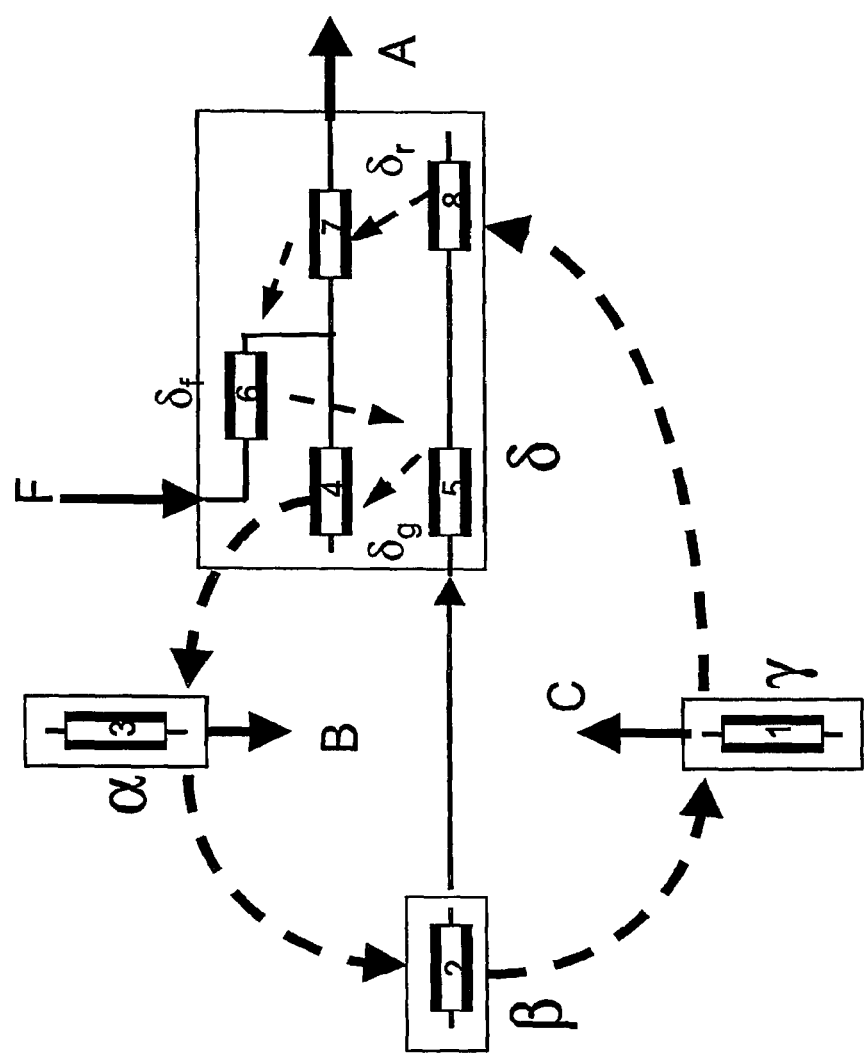
FIG. 6 shows a flow sheet of a specific "Continuous Gradient Purification Process"

For example, in FIG. 6 a specific design of section δ including five columns in this section is given. To have a larger number of columns in this section δ is most often advisable due to the fact that this section has to provide the full gradient sweep until the light impurities have been completely eluted in the batch column and pure desired product can be taken out of the batch column for some time until the heavy impurities start to break through.

Figure 7:
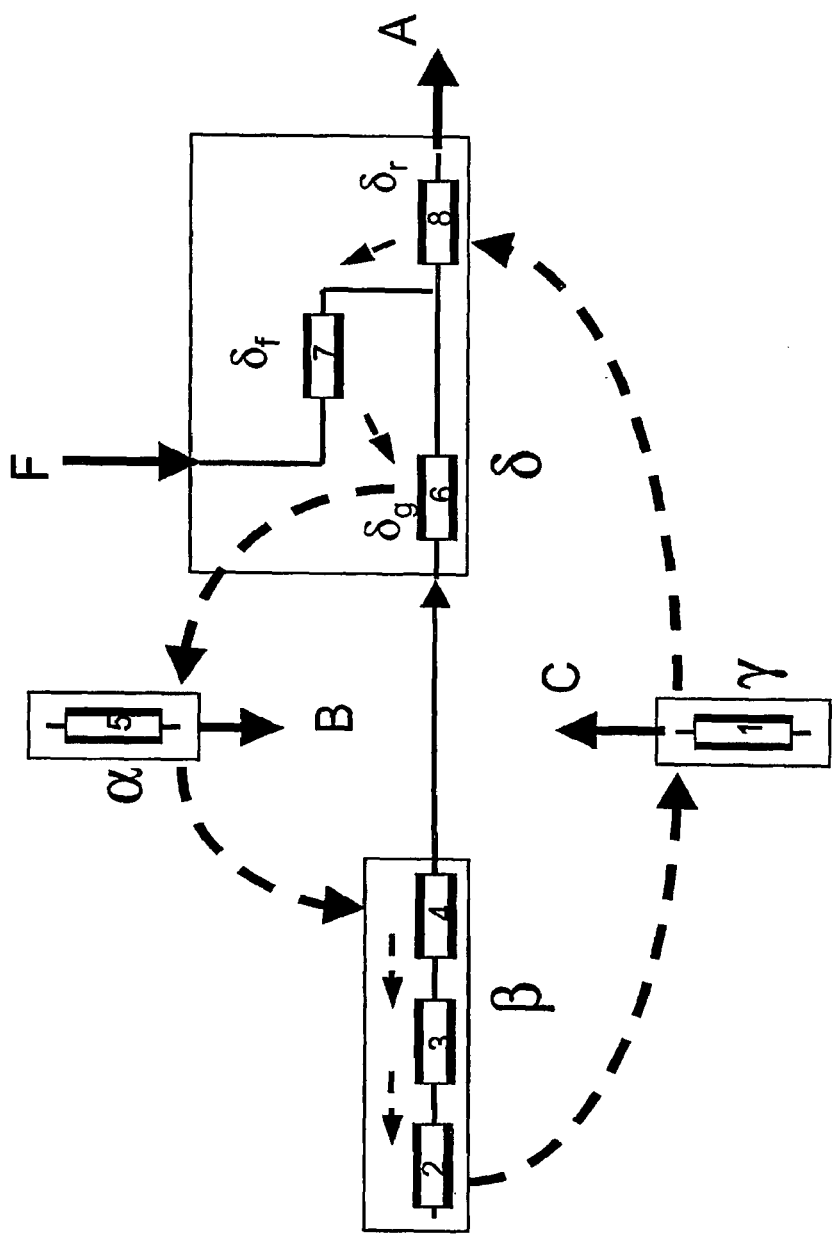
FIG. 7 shows a flow sheet of another specific "Continuous Gradient Purification Process"

FIG. 7 shows the possibility of having several columns in section β which are working in a countercurrent manner, so this section is actually structured closely analogous to am SMB arrangement.

Figure 8:
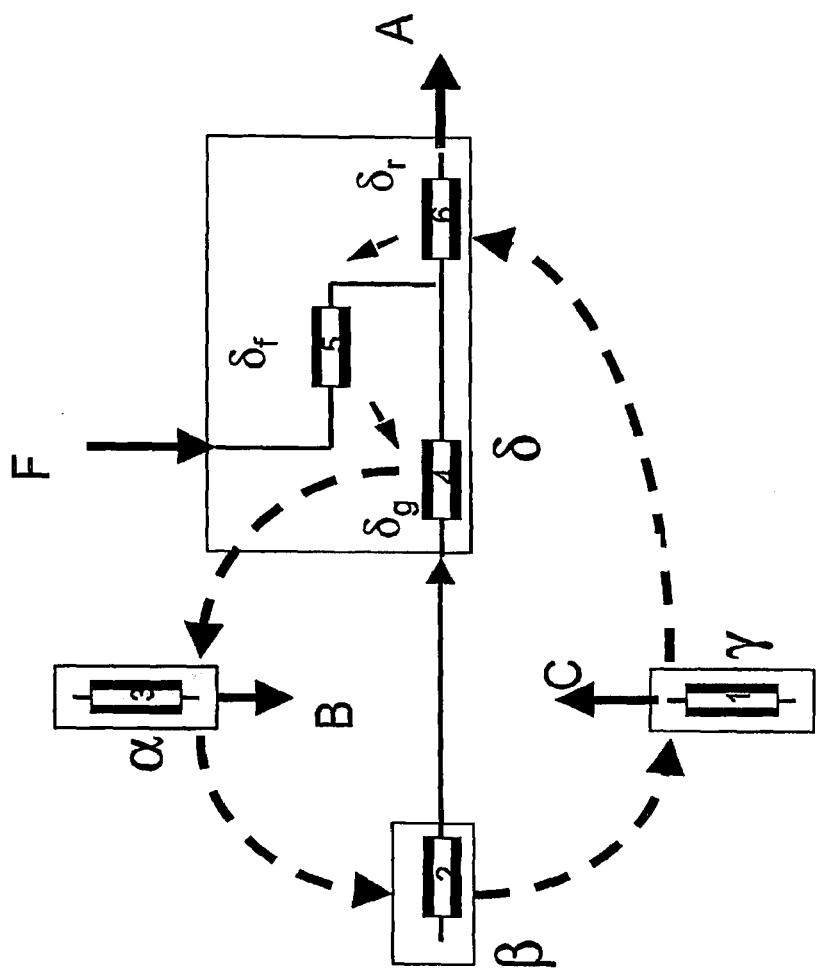
FIG. 8 shows a flow sheet of another specific "Continuous Gradient Purification Process"

In FIGS. 7 and 8 another variation of the section 6 is also shown, wherein 3 columns are used. To have an arrangement as the one displayed in FIG. 4, in FIG. 7 the outlet of column 7. is not connected to the inlet of column 8.

FIG. 6 shows an example of an 8 column system which has been used for experimental verification. It has to be pointed out that in principle in a setup as the one shown in FIG. 6 it would also be possible to connect the outlet of column 2. with the inlet of column 4.

Also within section δ a specific structure can be established. Usually it is advisable to have at least one column (first subsection $δ_f$), in this case column 6. which is used for loading the feed, and which has a low flow rate. This column can either directly remove light impurities out of the system or into another column of section δ. Another second subsection $δ_g$ within section δ is given by columns 4 and 5, which provide an inlet for taking up output of the second section β and which output to a further and third subsection $δ_r$. which consists of columns 7. and 8. in this specific case.

The second subsection $δ_g$ basically removes all light impurities A and makes sure that they are directly transferred to the third subsection. In addition to that, the second subsection $δ_g$ makes sure that the desired product B is perfectly positioned within column 4. just before the switch, when column 4. is moved to position 3. and that the full gradient is necessary to transport B of the proper position of the solid is run. In this context it has to be pointed out that this second subsection is responsible for driving the full gradient until the last parts of the light impurities reach the end of the last column in the section. Therefore the number of columns in this section might be adapted if this time is particularly long.

Specifically it is advisable not to connect the output of column 4 to the input of column in order to avoid that light impurities are washed into column 5 at the wrong position in the solid phase.

The third sub-section formed by column 7. and 8. comprises at least one inlet for taking up output of the second sub-section $δ_g$ and possibly at least one inlet for taking up output of the first sub-section $δ_f$, and at least one outlet, and it serves to make sure that B is kept in the system and that the light impurities are removed from the system. In the setup according to FIG. 6 the outlet of column 8 is formed by clean solvent.

FIG. 7 shows another set up, in which for better separation in section β three columns are arranged countercurrently. In FIGS. 7 and 8 the most simple structure of a substructure in section δ as detailed above in the context of FIG. 6 is given. In case of difficult separation from the light impurities, and set up according to FIG. 8 is preferred to a setup according to FIG. 4.

The generalized scheme may take many specific forms as for example:

If a pulse is fed, section δ requires one column less than if the feed were continuous.

If the heavy impurities adsorb much stronger than the intermediate product, section β contains no column.

For lucky cases the process can even be operated without applying solvent gradients.

It also has to be pointed out that the sections α, β, and γ may also be combined into one column in which in a timewise staged manner individual fractions which then equal the output of sections α, β and γ as given in FIG. 5 are taken out and fed to the input of the corresponding elements in FIG. 5.

For variable set-ups as the one proposed in this application it is very important to have generalised and simple schemes for setting up the parameters for running the system in a manner which is tailored to a specific purification problem. In the present case there is a very simple scheme and technique which, departing from a gradient batch chromatogram allows to find the parameters for the continuous process as proposed.

Figure 9:
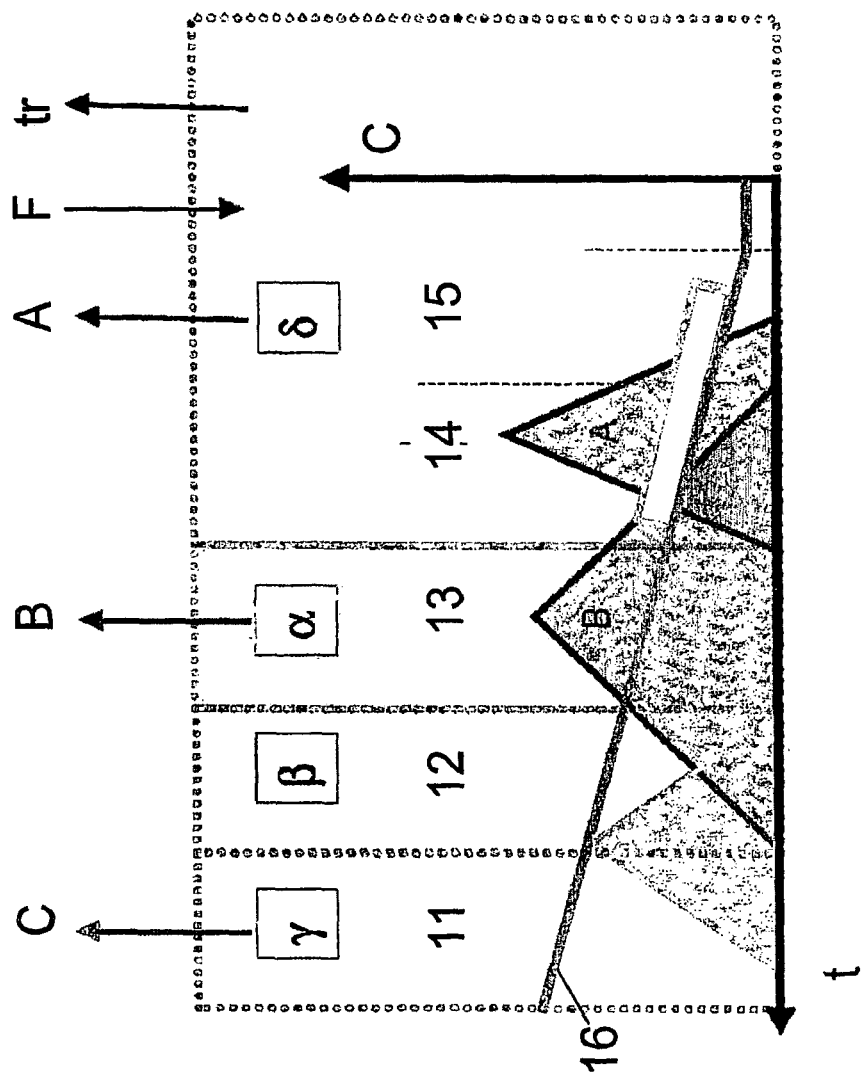
FIG. 9 shows a qualitative chromatogram and sections of the purification process.

The process can be easily designed from an experimental (or simulated) concentration profile as follows. Every section refers to a time interval as shown in FIG. 9. The tasks of the sections α-δ refer to the events happening in the corresponding time interval of the batch elution.

A concrete example is simulated to increase the understanding of the transfer from batch to continuous purification. In this example a solvent gradient (modifier gradient) from 170 g/l ACNL (Acetonitrile) to 190 g/l ACNL is carried out. Flowrate is 0.5 ml/min. Column volume 1.66 ml. The gradient starts at 0 min and ends at 25 min. 25 μl of 1 g/l raw Calcitonin is injected, in which the purities are Light1 (A1): 25%, Light2 (A2): 5% intermediate (B): 55%, heavy (C): 15%.

The desired yield is 60% and the purity is 82.9%, so that the intermediate fraction is taken from 26.8-31 min.

Figure 10:
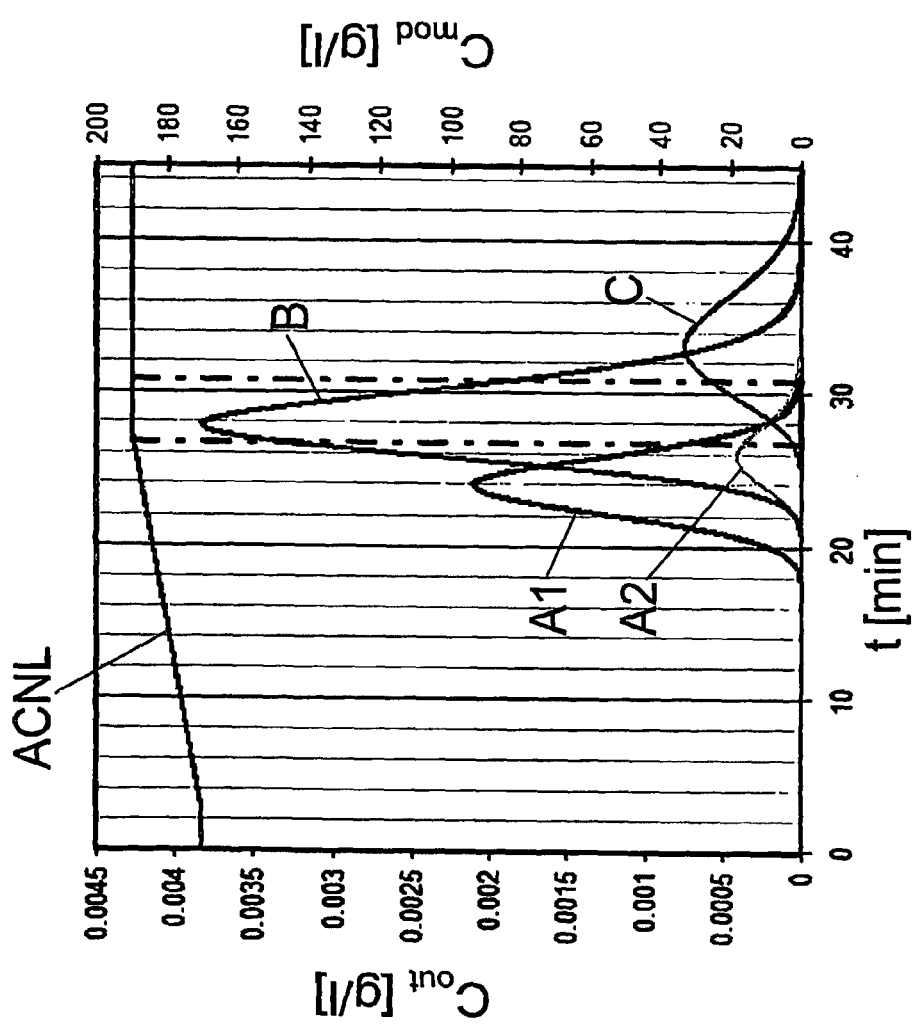
FIG. 10 shows a simulated gradient chromatogram to demonstrate the design of the continuous process.

This leads to a profile as given in FIG. 10.

Departing from such a batch gradient chromatogram, a continuous process is designed as follows:

7 columns are used, which have the same dimension as the single batch column.

The system in FIG. 6 is chosen for the example, but in the simulation a pulse is injected as feed and there is no continuous feed. Due to the pulse feed, column 6 is not necessary and not used.

The tasks of the sections are as follows:

Section α: do what happened between 26.8-31.0 minutes.

Section β: do what happened between 31.0-38.0 minutes.

Section γ: do what happened between 38.0-43.0 minutes.
Section δ: do what happened between 0.0-26.8 minutes and collect the outlet of section β. Get the feed into the system.

All tasks have to be finished within one switch time t*. The task of section δ requires the longest time, which is the reason for having 4 columns in that section. We define the following design parameters, which values correspond to the chromatogram:

TABLE 1

| Event | time (min) | Variable | mod. conc. at column inlet (g/l) |
|---|---|---|---|
| start | 0 | t_Start | 170 |
| A starts eluting | 18 | Start_A | 184.4 |
| B starts eluting | 22 | Start_B | 187.6 |
| Fractionation starts | 26.8 | Start_Frac | 190 |
| Fractionation ends | 31 | End_Frac | 190 |
| B ends eluting | 38 | End_B | 190 |
| All components are out | 45 | t_End | 190 |

The general procedure to calculate the switch time is as follows: for the setup shown in FIG. 6 the gradient from feeding until the time, where pure desired intermediate product breaks through shall be transferred to the columns 4 and 5. The column which is operated with a higher flow rate is limiting the process. In the example presented here, column 5 runs the longer part of the gradient (Start_A−t_Start=18 min) while column 4 runs the shorter part (Start_Frac−Start_A=26.8−18=8.8 min). Optimal with respect to the productivity would be, if column 4 and column 5 are operated with the same flow rates.

In this specific example it is decided to run in column 5 the part of the batch gradient until the light impurity starts to elute. So the required switch time can now be calculated as:

$$t^* = \frac{(\text{Start\_A} - \text{t\_start})Q_{batch}}{Q_{max}} = 4 \text{ min}$$

So the flow rates inside the columns have to be:

$$Q_1 > \frac{V_{Column}}{t^*}$$

$$Q_2 = Q_{batch}\frac{\text{End\_B} - \text{End\_Frac}}{t^*} = 0.875 \, \frac{ml}{min}$$

$$Q_3 = Q_{batch}\frac{\text{End\_Frac} - \text{Start\_Frac}}{t^*} = 0.53 \, \frac{ml}{min}$$

$$Q_4 = Q_{batch}\frac{\text{start\_Frac} - \text{Start\_A}}{t^*} = 1.1 \, \frac{ml}{min}$$

$$Q_5 = Q_{batch}\frac{\text{Start\_A} - \text{t\_Start}}{t^*} = 2.25 \, \frac{ml}{min}$$

$$Q_6 \approx Q_{Feed}$$

wherein, as mentioned above, here the feed is pulsed into column 5, so that column 6 is not used $$Q_7 \approx Q_4$$

$$Q_8 \approx Q_5$$

The solvent gradients are according to the mobile phase composition at the characteristic time at the column inlet (see table 1): With these values for the modifier concentrations and the internal flow rates, the input parameters for the columns can be calculated.

TABLE 2 mobile phase streams at the column inlets:

| Column | conc. modifier at t = 0 | conc. modifier at t = t* | | ml/min |
|---|---|---|---|---|
| 1 | Arbitrary, the task has to be fullfilled | Here 400 g/l isocratic Pump 1 | | 0.85 |
| 2 | 190 g/l | 190 g/l | Pump 2 | 0.88 |
| 3 | 190 g/l | 190 g/l | Pump 3 | 0.53 |
| 4 | 184.4 g/l | 190 g/l | Pump 4 | 1.10 |
| 5 | 157.1 g/l | 184.4 g/l | Pump 5 | 1.37 |
| 6 | Arbitrary, the task has to be fullfilled | Not used in the simulation | | — |
| 7 | Arbitrary, the task has to be fullfilled | Connected with outlet of Col. 4 | | 0.0 |
| 8 | Arbitrary, the task has to be fullfilled | Connected with outlet of Col. 5 plus 0.03 ml/min of pure acetonitrile Pump 6 | | 0.03 |

Figure 11:
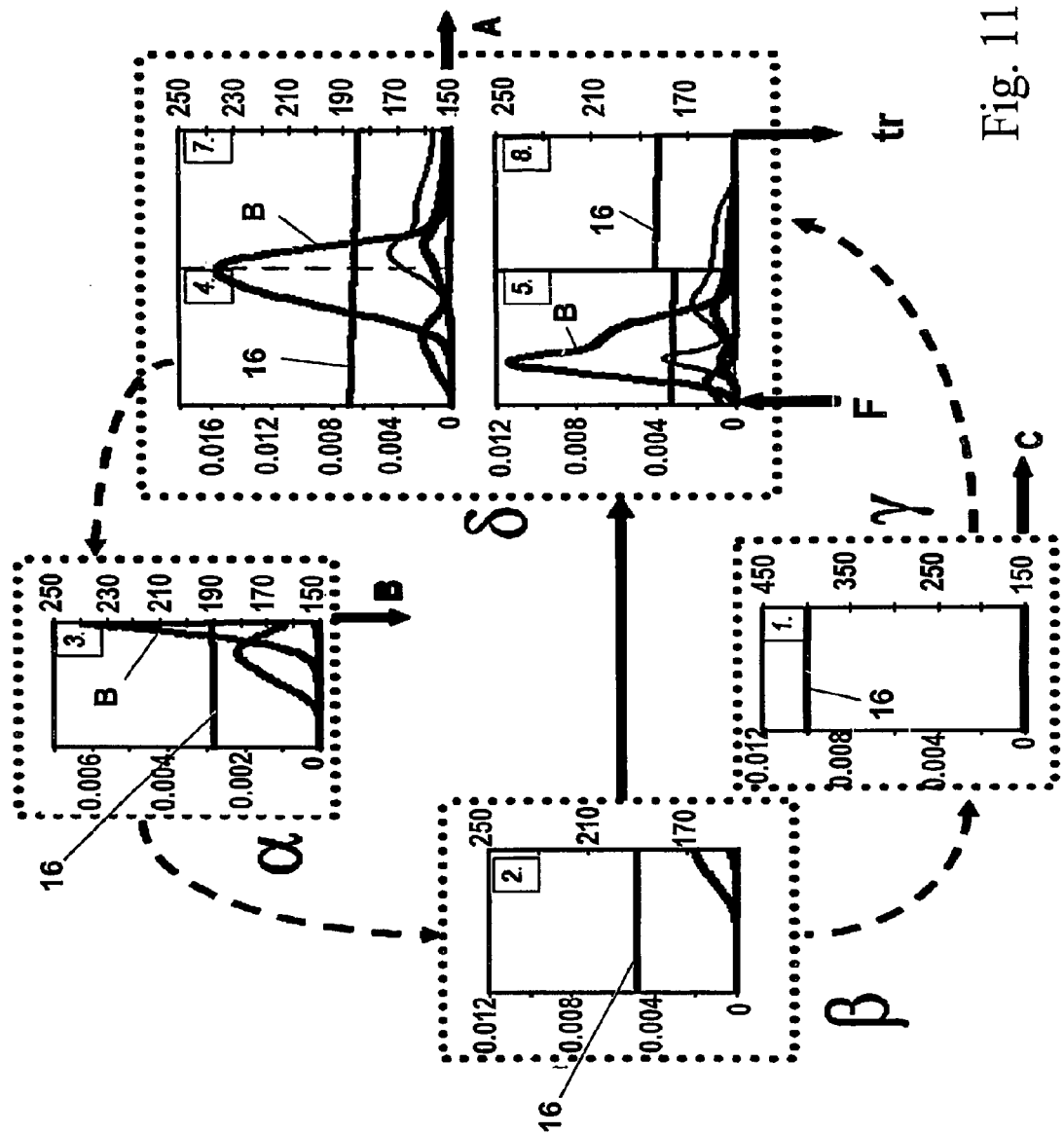
FIG. 11 shows a process simulation in the middle of a switch. It can be seen that column 1 is already cleaned completely.
Figure 12:
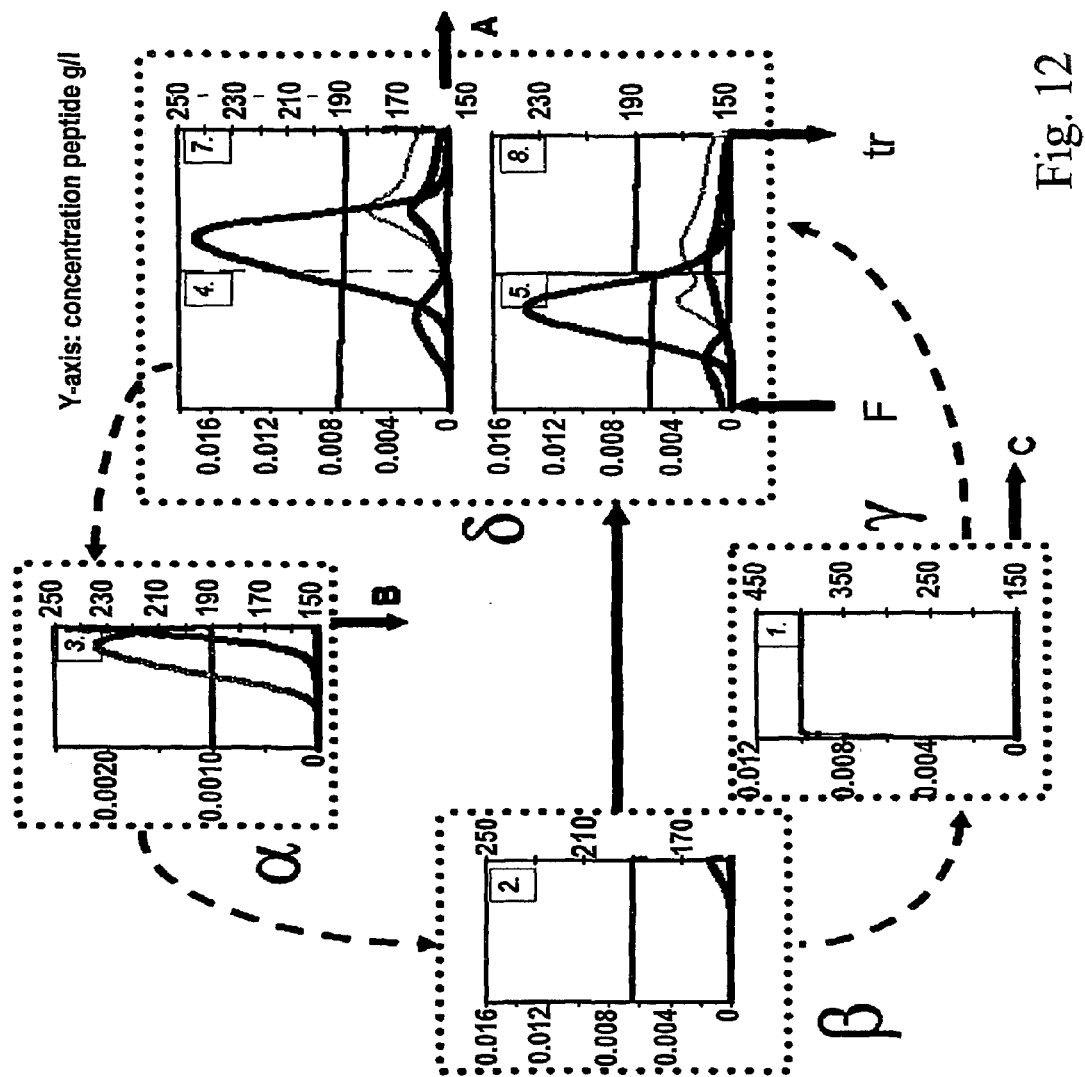
FIG. 12 shows a process simulation before a switch.
Figure 13:
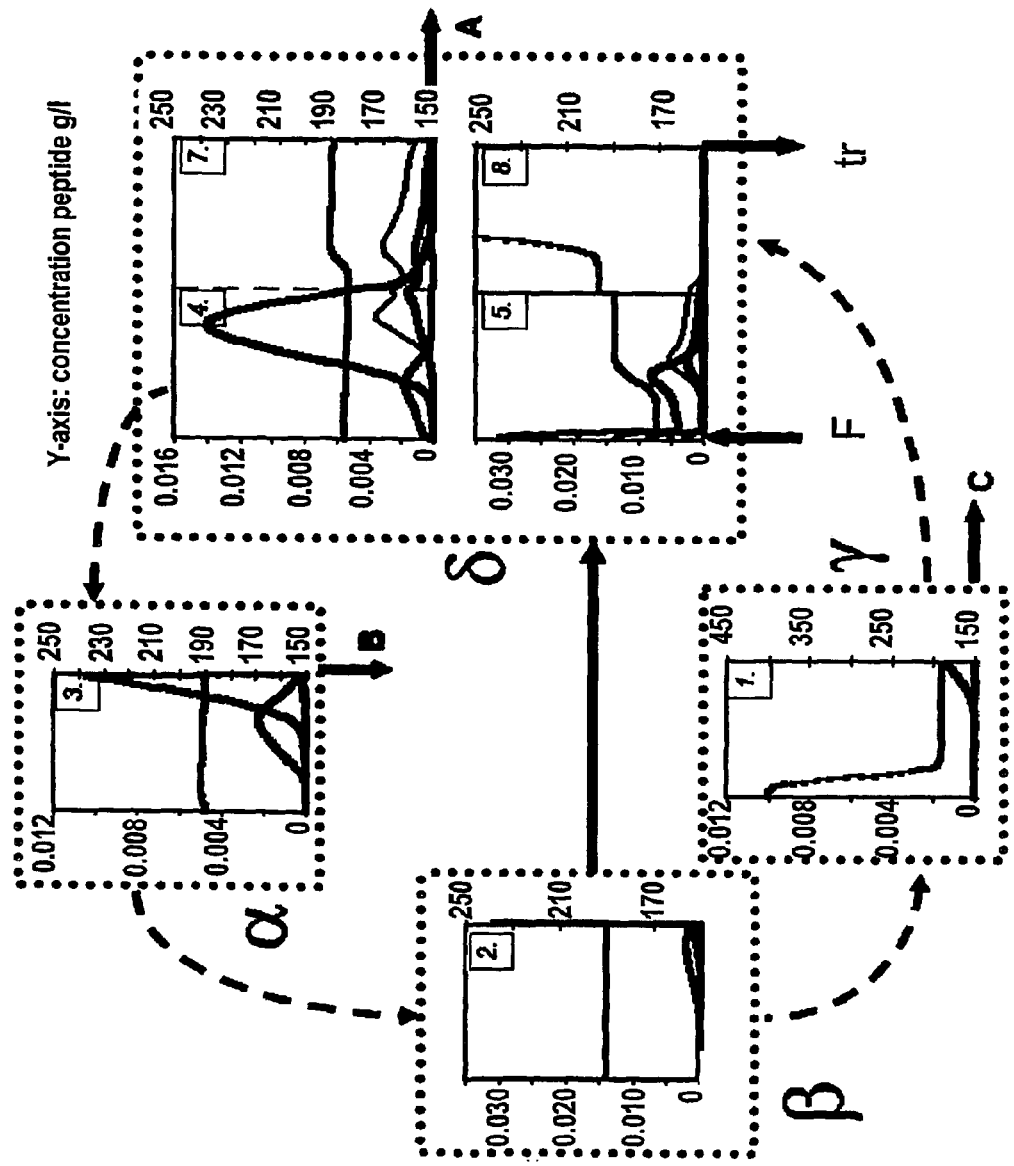
FIG. 13 shows a process simulation after a switch.

The simulation of the continuous process is shown in FIGS. 11-13. The concentration profiles inside the sections are shown before (FIG. 12), after (FIG. 13) and in the middle (FIG. 11) of a switch in steady state situation. On the left y-axis the concentration of the peptide is given in g/l, and on the right y-axis the concentration of the modifier is given in g/l.

The yield in this simulation is ca. 99.95% and the purity is 85.2%. A comparison with the batch process, from which the continuous process has been designed is shown in table 3.

TABLE 3

| | BATCH | CONTINUOUS |
|---|---|---|
| YIELD | 60% | 99.95% |
| PURITY | 82.8% | 85.2% |
| NUMBER OF COLUMNS | 1 | 7 |
| NUMBER OF PUMPS | 1 (gradient pump) | 6 (gradient pumps) |
| PRODUCTIVITY mg purified product per ml Column and min | 0.00070, calcuated with End_Frac = 32 min and with the max. flowrate of 2.25 ml/min | 0.000296 2.36 times smaller |
| ml solvent/ mg feed | 900 ml/mg (no equilibration taken into account) | 761.6 ml/mg |

The advantages of the continuous process become very clear, although in this example the productivity of the batch process is ca. 2 times larger than for the continuous process. A further decrease of solvent consumption is possible. But in this example the continuous process has been directly transferred from the batch chromatogram. It is not optimized yet. A slight change of the flow rates in column 4 and 5 can decrease the minimal switch time to 3 minutes, so that the productivity would increase by 33%. The potential of optimizations has not been fully explored yet.

The higher the quality constraints like yield and purity become, the more valuable the continuous process becomes. This is most important for very expensive solutes, like for bio molecules.

It is well known, that batch processes require a high number of theoretical stages. So the example above must also compare the continuous process with a batch process in the case, that the batch column consist of the same amount of resin than the continuous multicolumn plant.

Figure 14:
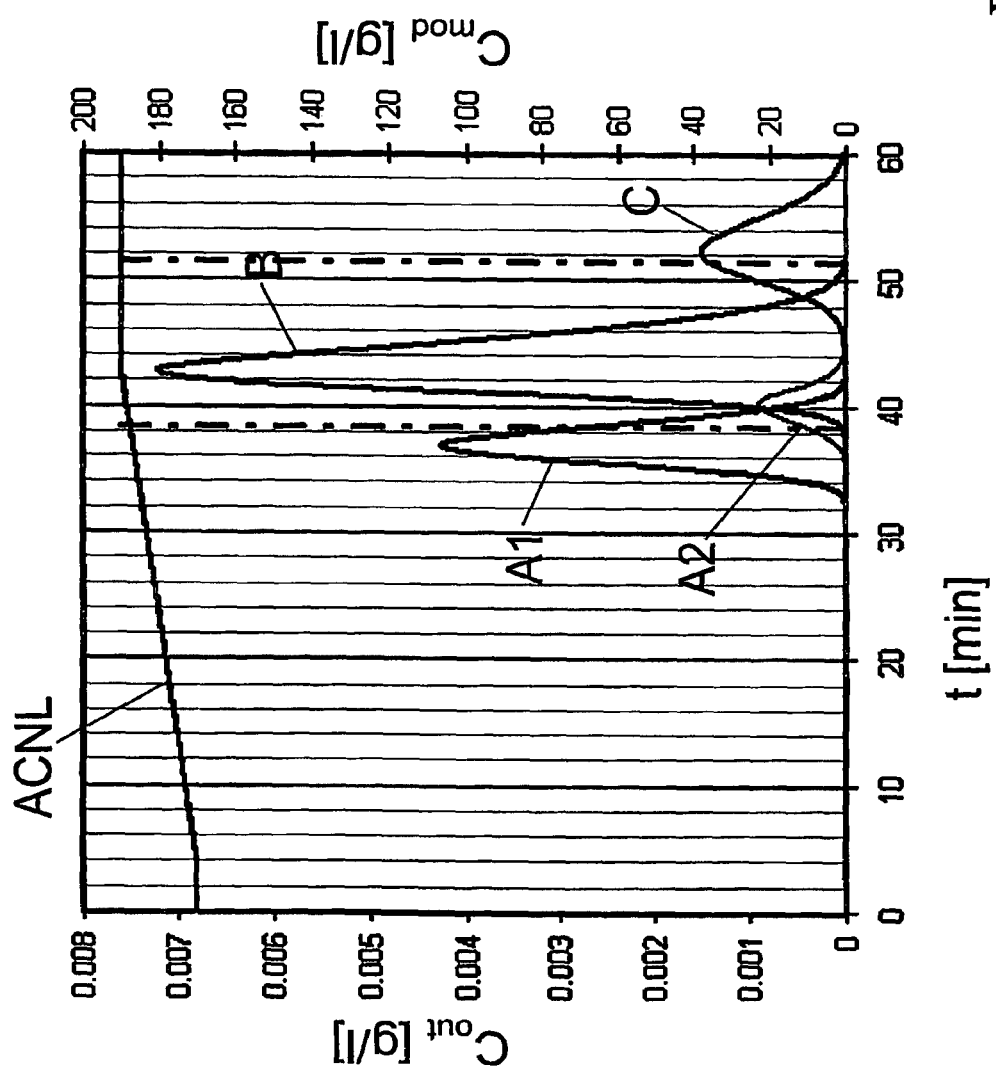
FIG. 14 shows a simulated gradient chromatogram for the batch elution with maximal flow rate of 2.25 ml/min and 7 short columns in a row with a purity of 79.0% and a yield of 100%.

FIG. 14 shows the batch elution carried out with the maximum flow rate of 2.25 ml/min on 7 single columns in a row (7 times more stages and 7 times higher load). It can be seen that the purity for 99.95% yield is only 79%. If the required purity is 85.2%, the yield of the batch would be 99.6%. The productivity of the batch with 7 columns in a row is only 54% compared to the continuous process. See table 4.

TABLE 4

|  | BATCH | CONTINUOUS |
|---|---|---|
| YIELD | 99.95% | 99.95% |
| PURITY | 79.0%% | 85.2% |
| NUMBER OF COLUMNS | 7 | 7 |
| NUMBER OF PUMPS | 1 (gradient pump) | 6 (gradient pumps) |
| PRODUCTIVITY mg purified product per ml Column and min ml solvent/ mg feed | 0.000159, calcuated with End_Frac = 52 min and with the max. flowrate of 2.25 ml/min 900 ml/mg (no equilibration taken into account) | 0.000296 1.86 times larger 761.6 ml/mg |

Because the total pressure loss of a chromatographic column is proportional to the column length, the maximum flow rate for the long column will be much smaller than the maximal flow rate for the short column, which will further decrease the productivity of the batch elution.

Experimental Verification—Purification of Calcitonin

Figure 15:
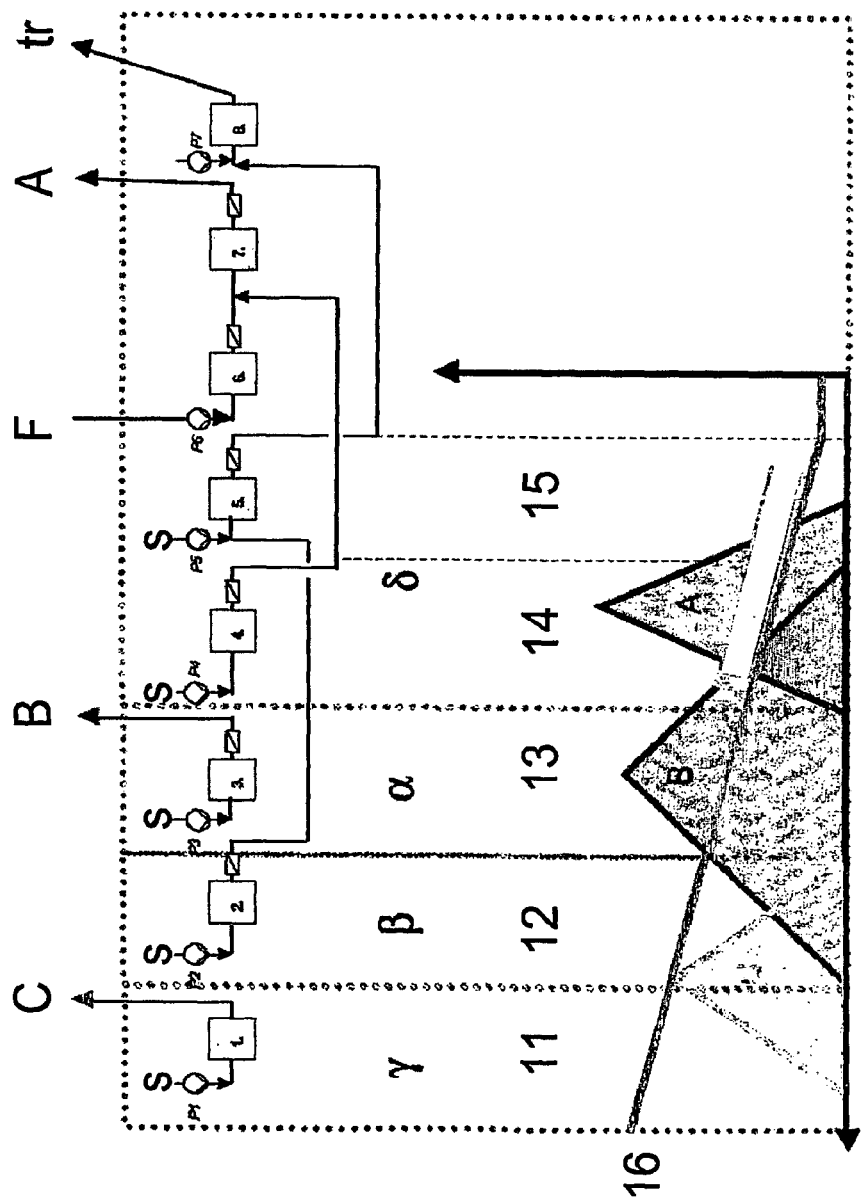
FIG. 15 shows a flow sheet of the 8 column process used for the verification and qualitative chromatogram.

The novel process has been experimentally verified with an 8 column open loop system as shown in FIG. 15. Input parameters for the experiment are taken from a simulation. The figure below is equivalent to FIG. 6. The chromatogram as well as the solvent gradient is split into tasks, fulfilled by the four sections α-β-γ-δ. The process is fully analogue to the gradient batch elution, but enables countercurrent recycling of the non pure side-fractions in section δ and between section β and δ.

The 8 columns inside the four sections have the following tasks:

Section γ: (1 Column)
Column 1. wash component C out of the system.
Section β: (1 Column)
Column 2. wash out a small valuable amount of B, which is contaminated by C. To recycle B, the liquid outlet stream of column 2. is washed into column 5.
Section α: (1 Column)
Column 3. wash out the purified product B. Fresh solvent is used to guarantee the highest possible purity.
Section δ: (5 Columns)
Column 4. wash out a small, but valuable amount of B, which is contaminated by A. In this example fresh solvent is used. Another task of column 4. is the partial separation between C and B. It makes sense to run column 4. under linear gradient conditions. The eluted solutes are washed into Column 7. for recycling.
Column 5. wash out the major part of A into column 8. The solvent used here consist of recycled solvent coming from column 2 (section β). plus weak solvent from pump 5. which is required to adjust the accurate modifier concentration. Another task of column 5. is the partial separation between C and B.
Column 6. is the feeding column. Here the flow rate should be as small as possible to get a large number of theoretical stages and a narrow loading profile.
Column 7. is a recycling column. Its task is: a). catch A+B from the outlet of column 4. and b.) separate as well as possible A from B. The solvent used here consist of recycled solvent coming from column 4. plus weak solvent from pump P7. which is required to adjust the accurate modifier concentration.
Column 8. is also a recycling column. Its task is: a). catch A+B from the outlet of column 5. and b.) separate A from B as good as possible. The solvent used here consists of recycled solvent coming from column 5. plus weak solvent from pump P8.

It is sometimes useful to run a negative solvent gradient in column 7 or 8 to get better stability in the case of nonlinear adsorption isotherms. Also column 2 should be operated with a negative solvent gradient (start at high modifier concentration, end at low modifier concentration).

The plant used for the experiments consists of 3 "Äkta-Explorer Basic" systems, which are equipped with several additional multiposition valves and additional gradient pumps. The software for the three Äkta machines is "UNICORN" from Amersham and the overall control of the three UNICORN systems running simultaneously is realized with the software "Genesis".

Figure 16:
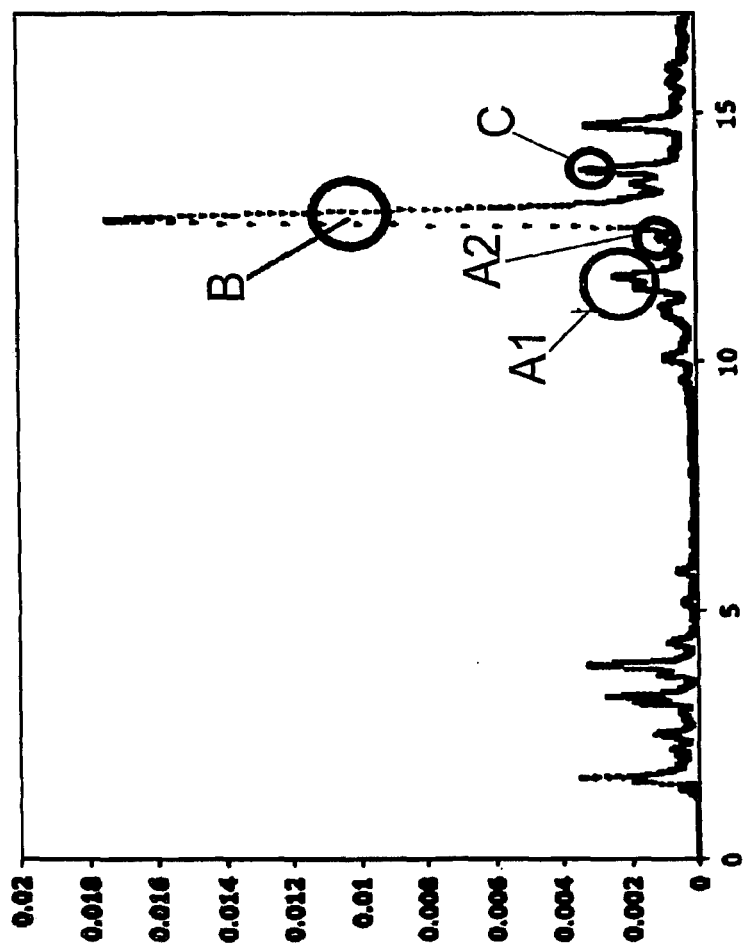
FIG. 16 shows the gradient analysis of the feed with the analytical ODS-Column ZORBAX ODS SB-300.

The mixture being purified is the polypeptide Calcitonin with a molecular mass of 3432 g/mol taken out of the production process before reversed phase purification. An analytical chromatogram of the feed is shown in FIG. 16. The feed consists of ca. 46% Calcitonin, ca. 19% heavy impurities and 35% light impurities. Calcitonin is the intermediate fraction "B".

The columns inside the continuous plant used to purify the peptides are packed with SOURCE RPC 15 from Amersham. Column dimensions are 100×4.6 mm. Mobile phase is water/ $H_3PO_4$ and acetonitrile. The number of theoretical stages per column is around NTP=100.

Experimental parameters like flow rates and modifier concentrations are based on the simulation. The experimental parameters chosen for the verification are:

| | |
|---|---|
| Solvent A: | 998.5 g/l water, 1.17 g/l $H_3PO_4$ (85%) |
| Solvent B: | pure Acetonitrile |
| Feed: | 0.9 g/l raw Calcitonin with 43% purity solved in A |
| Switch time: | t* = 6 min. |
| Pump 1 | 0.25 ml/min, from 60.0% B to 30.1% B in 0.73 t* |
| Pump 2 | 0.75 ml/min, from 24.31% B to 29.13% B in t* |
| Pump 3 | 0.13 ml/min, from 24.31% B to 24.31% B in t* |
| Pump 4 | 0.15 ml/min, from 24.31% B to 24.31% B in t* |
| Pump 5 | 0.13 ml/min, from 24.31% B to 1.29% B in t* |
| Pump 6 | 0.045 ml/min, (feed into col. 6, 0.03 ml/min pure B into col. 8) |

It can be shown by the online UV-signals and the conductivity signals of the outlets from column 1 (C), 3 (B) and 7 (A) that the signals start to reach a periodic constant pattern after ca. 150 min. The system requires ca. 800 min to reach steady state.

The purity of Calcitonin in steady state is 85%, which corresponds to the value predicted by simulations. The yield agrees also with the simulation and has a value of around 97%.

Figure 17:
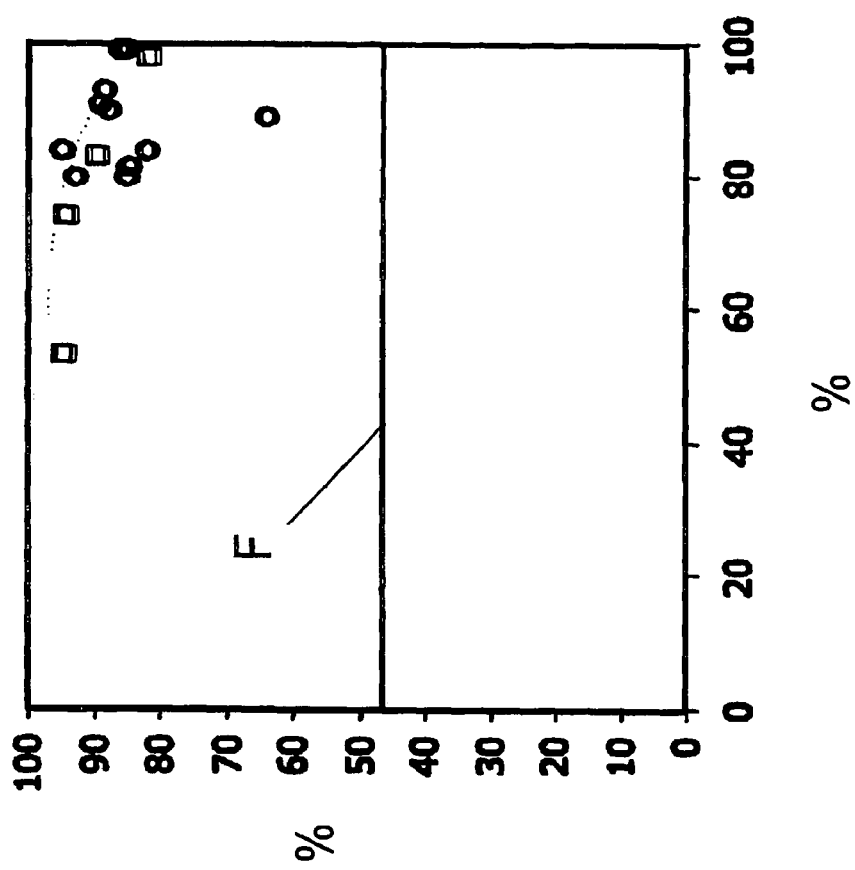
FIG. 17 shows the relation between yield and purity for slightly different operating conditions.
Figure 18:
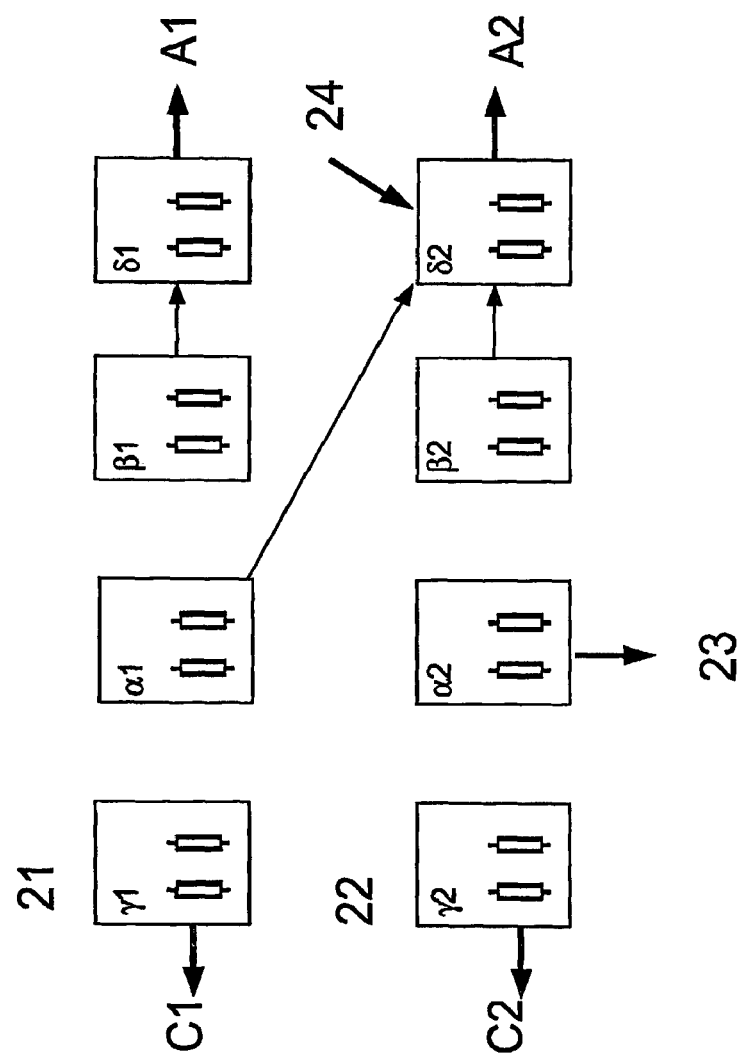
FIG. 18 shows two purification systems in a row.

16 experiments have been carried out. A diagram for purity and yield of these experiments is shown in FIG. 17. Purity in % is given as a function of the yield in % (x-Axis).

Sequential Setup

Usually one type of chromatographic separation is not sufficient to completely purify a biomolecule or to fulfil safety restrictions. Then two systems in series can be used as for example Ion Exchange Chromatography (IEX) and afterwards Hydrophobic Interaction Chromatography (HIC). Two purification systems can be put in a row, e.g. see FIG. 17. The feed F is introduced into section δ1 of the first system. The purified intermediate fraction from system 1 is loaded into the δ-section of system 2. Salt or organic modifier is also introduced into this section δ2 of system 2. It is possible to pulse the outlet of al within for example ⅓ of a switch. The remaining ⅔ of the switch can be used to wash tracers out of the loading column in section δ2. Because both processes are continuous, the two systems can operate with different switch times. System 2 can be designed from a chromatogram of the partly purified outlet from section α1.

The Gradient Purification Process can also be operated in quasi-continuous or half-continuous mode. Then up to 3 columns less, i.e. e.g. down to two or three columns, can be used to fulfil the purification task. This can increase the productivity compared to the full continuous process as given above for the case that the purified product stream and the feed flow rate are small compared to the other flow rates. Furthermore, reduction of the number of columns simplifies the setup since the system requires almost identical columns for reliable operation, and packing of a large number of almost identical columns can be burdensome.

Combination of sections α, β and γ:

The most obvious setup for quasi- or semi-continuous operation is already mentioned above in that the sections α, β, and γ may also be combined into one column in which in a time wise staged manner individual fractions which then equal the output of sections α, β and γ as given in FIG. 5, are taken out and fed to the input of the corresponding elements in FIG. 5.

Figure 19:
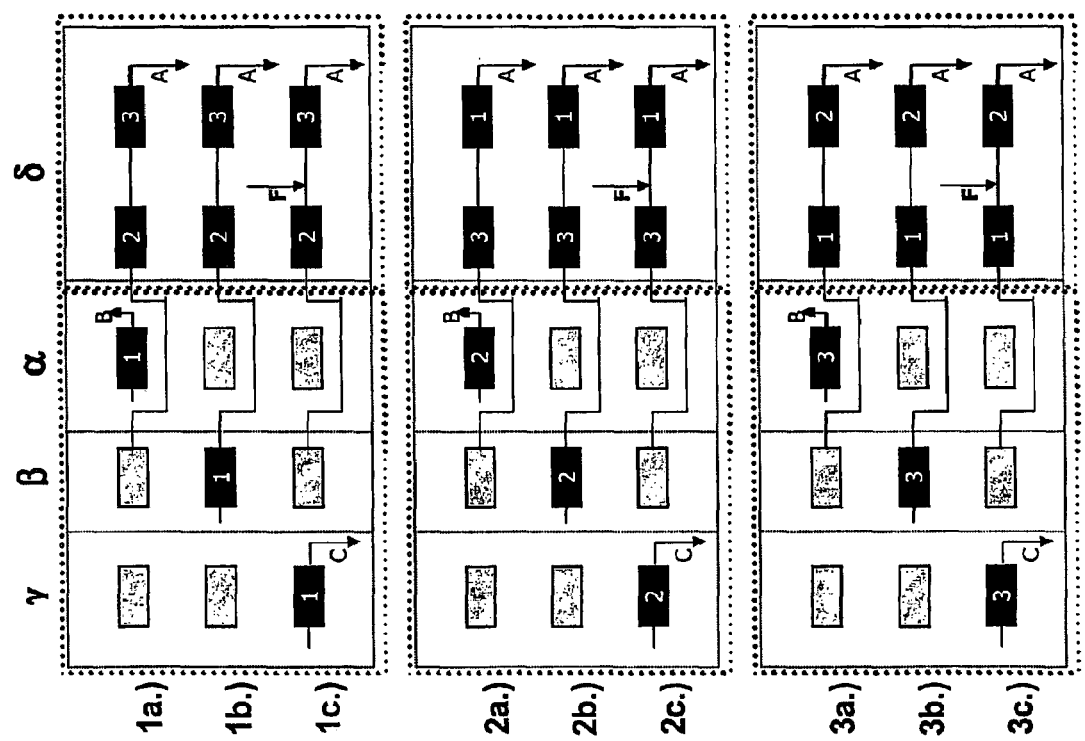
FIG. 19 shows a scheme of a "5-column unit" operated with only 3 columns, wherein the sections α,β,γ are combined in one column.

Such a possible set up, embodying a flow-sheet as given in FIG. 5 but with only one single column as section β, is given in FIG. 19. In this case, the sections α,β,γ are combined in one column. A black box in FIG. 19 means that there is a column fulfilling this function, a shaded one means that there is no column fulfilling that position. The scheme as displayed in FIG. 19 switches according to the following scheme: (1a-1b-1c)-(2a-2b-2c)-(3a-3b-3c)-(1a-1b-1c)-(2a-2b-2c)- . . . etc.

This figure shows that the functions of individual sections does not necessarily have to be fulfilled concomitantly, i.e. synchronously by individual columns, but that is well possible to fulfil the individual functions in a staged manner, as one can see from FIG. 19, steps 1a)-1c), in which sequentially column 1 fulfils the function of section α (step 1a), a then the function of section β (step 1b) and finally the function of section γ (step 1c). All these steps 1a)-1c) are carried out within one switch time. After this first switch time, so after the steps 1a-1c), the position of the columns 1-3 is cycled leading to the desired counter currency of the system.

The concept of combining sections α, β, and γ can be also applied to other column configurations, as for example to the 8 column setup (see e.g. FIG. 6), so that it would be reduced to only 6 columns.

Combination of pairs of sections in single columns:

Another very attractive way to use a smaller number of columns is the pair wise combination of sections, so e.g. the combination of section δ+α and section β+γ or more precisely into pairs γ+β; α+δ$_g$; δ$_f$+δ$_r$; or equivalently β+α; δ$_g$+δ$_f$; δ$_r$+γ.

In FIG. 20a) the 6-column setup according to FIG. 4 is shown and the sections embodied by each of the single columns are indicated in the figure. Specifically, the following tasks are fulfilled by the columns with reference to the numbering:
1. get all the heavy impurities C out of the column
2. get all the intermediate product B out of this column but keep the heavy impurities C in this column
3. make sure no heavy impurities C get out of this column but only the intermediate product B 4. get all light impurities A out of the column but keep the intermediate product B in the column
5. get the feed F into the column and the first light impurities A out of the column
6. make sure no intermediate product B leaves the column and remove the tracers from the column.

Figure 20:
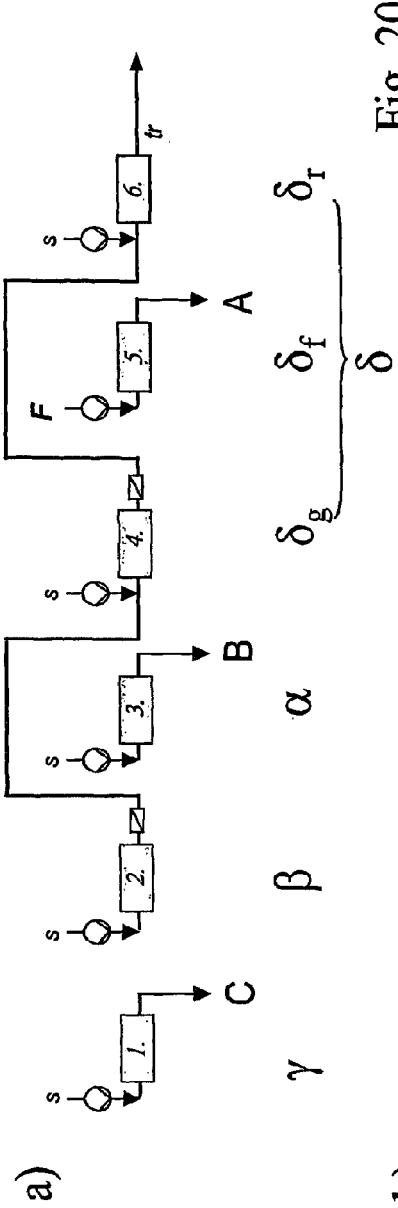
FIG. 20 shows a continuous 6-column unit with countercurrent-lane and batch-lane.
Figure 20:
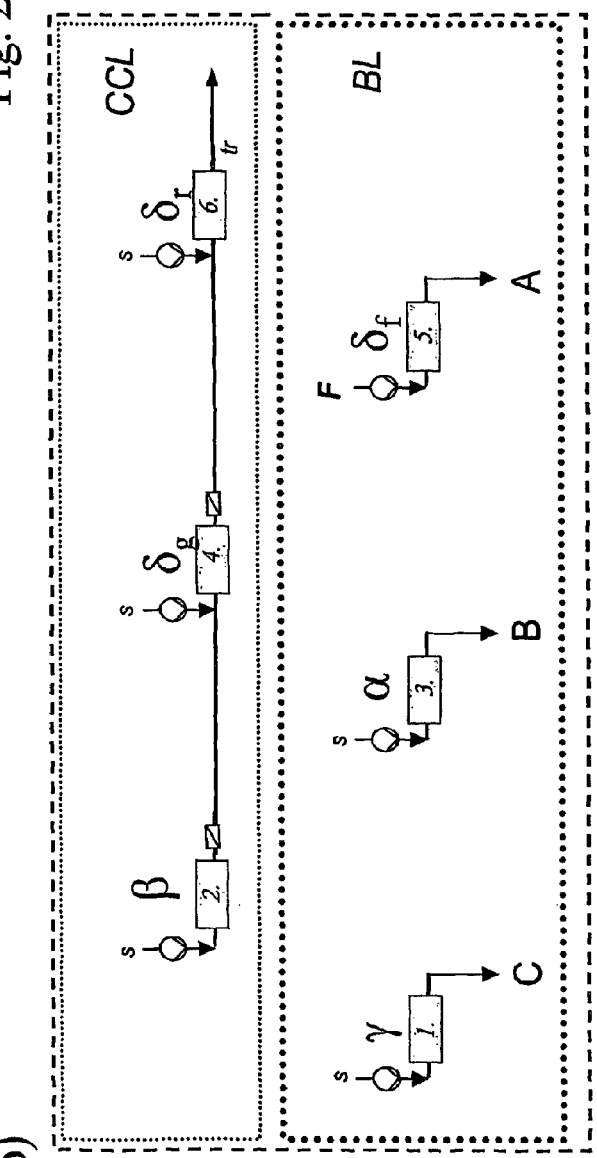

In FIG. 20 b), the 6 column setup is split into 3 interconnected and 3 non connected columns, which is identical to the 6 column setup drawn in FIG. 20a). The lane with the 3 interconnected columns is called "CCL" (CounterCurrent-Lane) and the one with the non connected columns is called "BL" (Batch-Lane).

Figure 21:
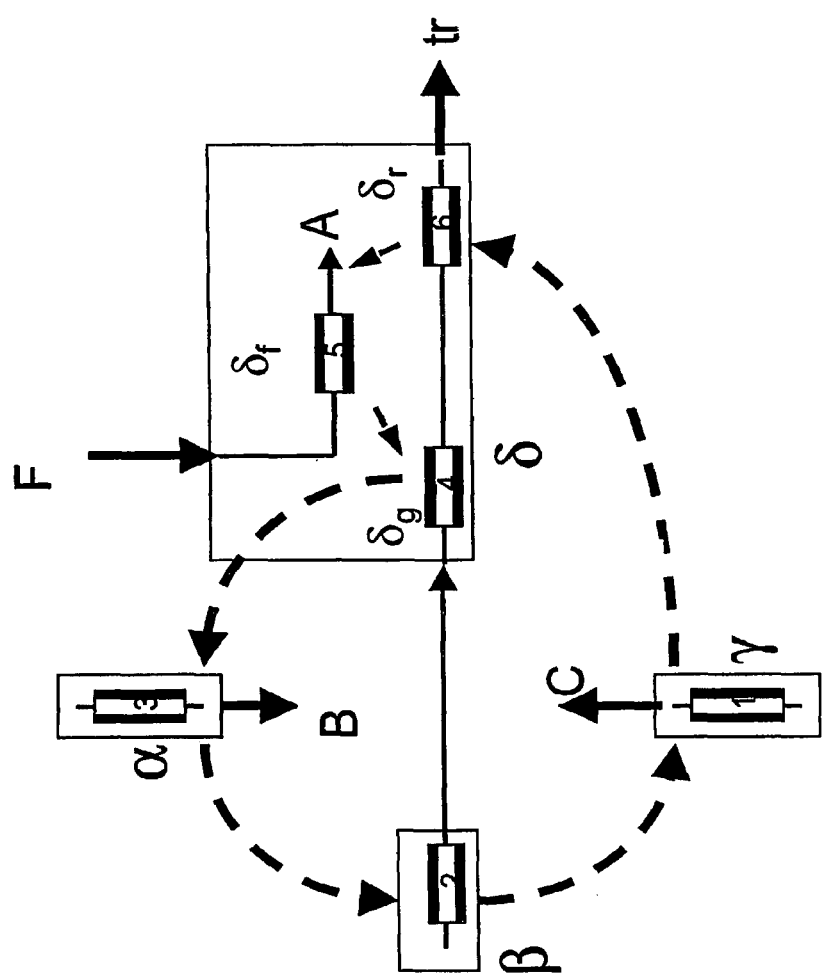
FIG. 21 shows a flow sheet of the specific "Continuous Gradient Purification Process" as displayed in FIG. 20.

The general topography of the setup according to FIG. 20 is given in FIG. 21.

The CCL consists of column positions 2,4,6 (β,δ$_g$,δ$_r$) and the Batch-Lane consists of column positions 1,3,5 (γ,α,δ$_f$). It is obvious, that, when the 6 column system switches between the two states CCL and BL, all columns of the CC-Lane become columns of the "batch-lane" and all columns of the batch-lane become columns of the CC-lane. The local switch time of both lanes is equal to the overall switch time t*. That makes the overall process continuous. The batch columns and the countercurrent columns are operated in the same plant at the same time.

Figure 22:
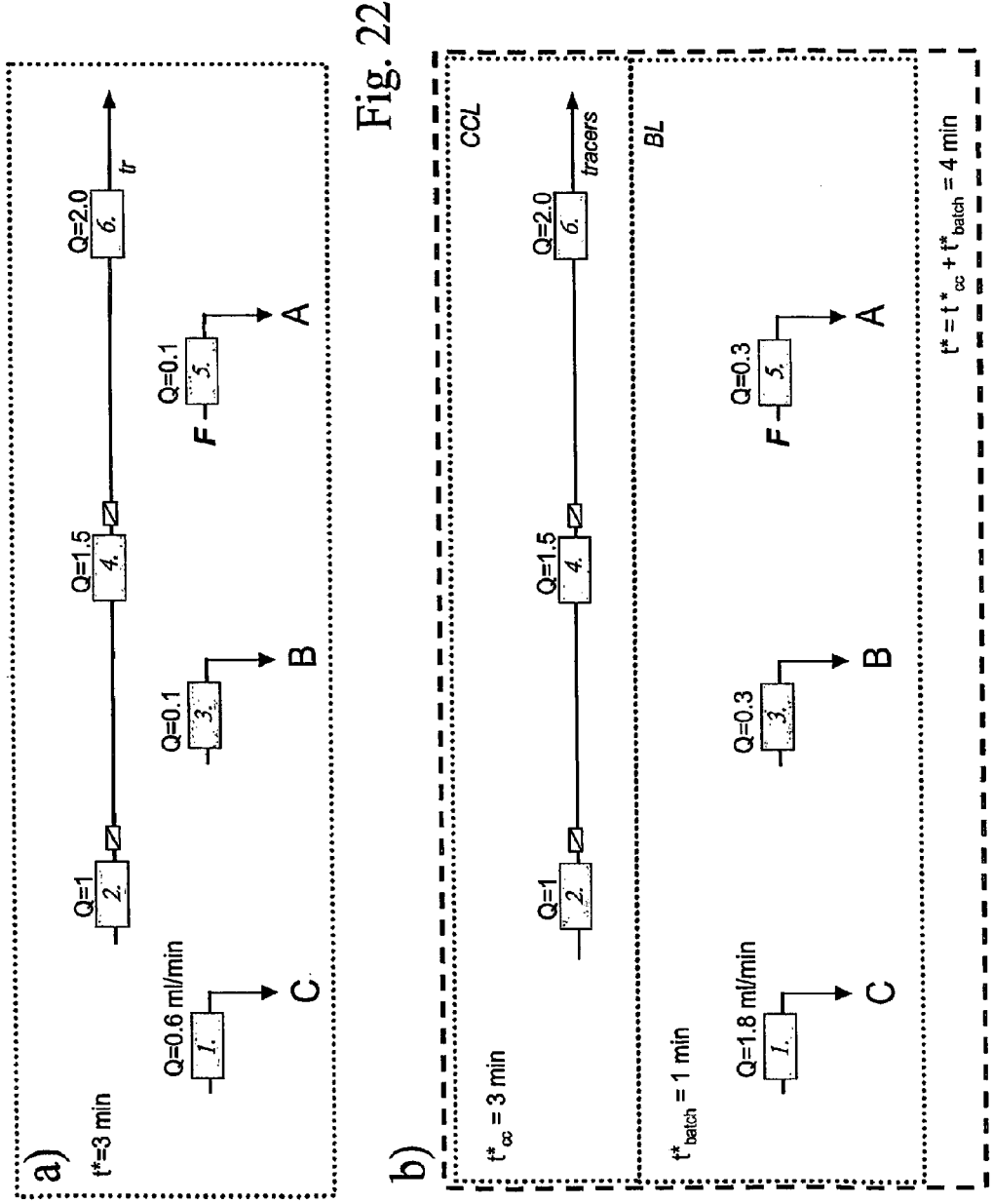
FIG. 22 shows the operation of the setup according to FIG. 20 with only three columns for specific experimental values.

To show the effects of such a reduction, an example shall be discussed: In FIG. 22, the upper part a) shows the 6 column process with a switch-time of 3 minutes. In this example the maximum flow rate in a single column is assumed to be 2 ml/min. So column 6 is limiting the flow rate and the productivity.

As already mentioned, both switch times must be equal to have a "fulltime" continuous process. Since there is no liquid stream between the two lanes BL and CCL, the lanes are independent from each other.

As a consequence it is attractive to use only 3 columns instead of 6 columns for the whole process and to start with the batch-lane, but to stop all flow rates in the batch lane, when the 3 columns are switched to the CC-lane. The same is valid for the CC-lane. When the 3 column are switched back to the batch lane, the flow rates of the CC-lane are set to zero.

So every column takes over the function of two sections, and these functions are fulfilled in a time wise staged manner instead of fulfilling the functions synchronously.

The local processes are still continuous, but they stop operation, while the other lane is active. So the overall process is not fully continuous anymore but quasi-continuous.

In the upper case the productivity is assumed to be 100%.

The switch-times of the batch-lane can now be decreased to for example 1 minute as shown in FIG. 22 b), leading to a total switch time of 4 minutes. Then the highest flow rate in the batch-lane would be 1.8 ml/min (<2 ml/min=Q$_{max}$), which is close to the maximum flow rate of the system.

Now one has two independent multicolumn switching processes with different switch times, which are operated alternatingly. The switch time of the CC-lane is 3 minutes and the switch time for the batch-line is 1 min.

The overall switch time is increased to $$t^* = t^*_{batch} + t^*_{C.C.}$$

but the number of columns is decreased from 6 to 3. So in this example the productivity of the process is even increased by 50%, since the productivity is given by $$P = 100\% \cdot 3/(3+1) \cdot 6/3 = 150\%.$$

Figure 23:
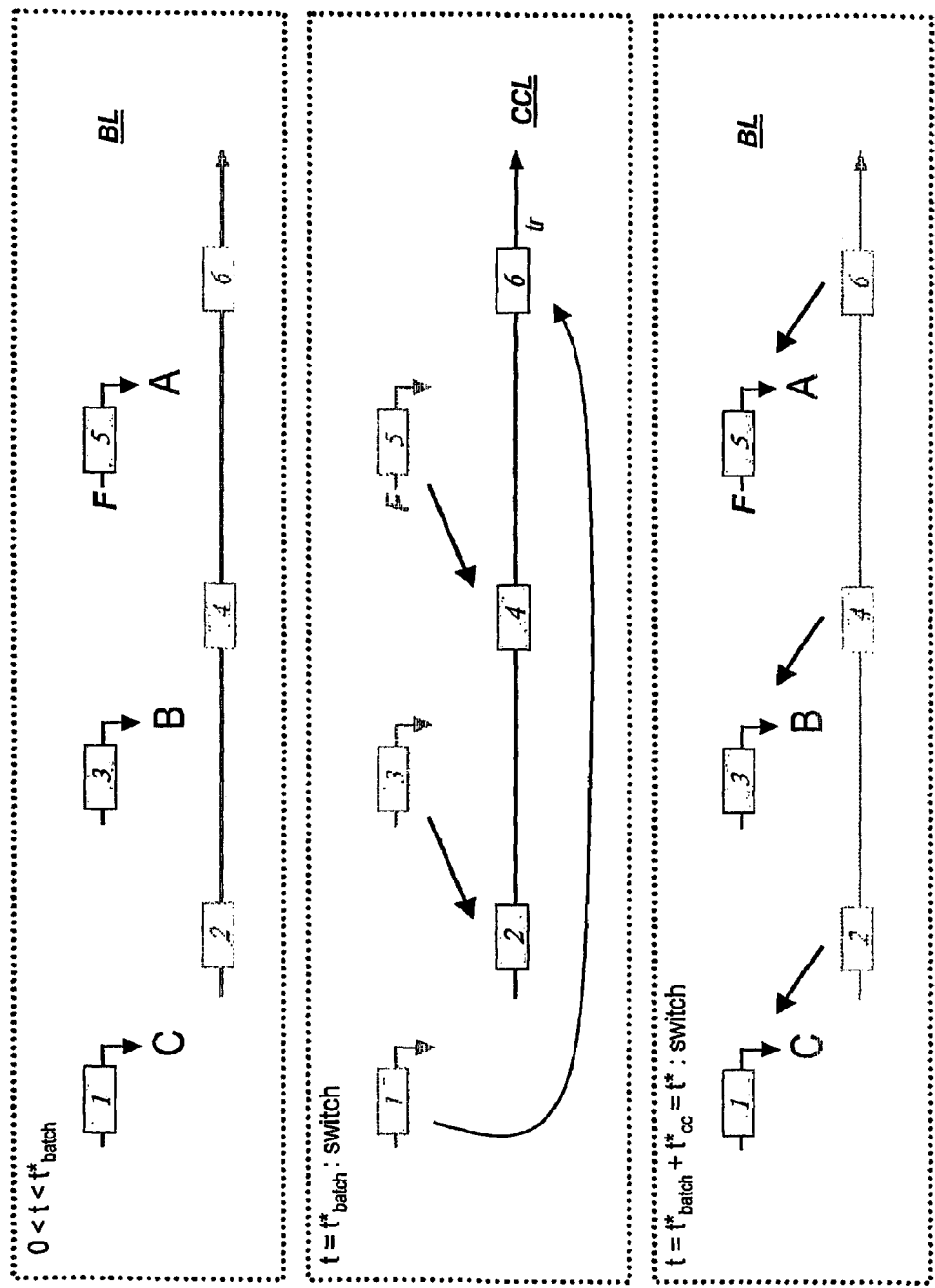
FIG. 23 shows the switching scheme of the setup according to FIG. 20.

The general switching scheme of a setup according to FIG. 22 is indicated schematically in FIG. 23.

Figure 24:
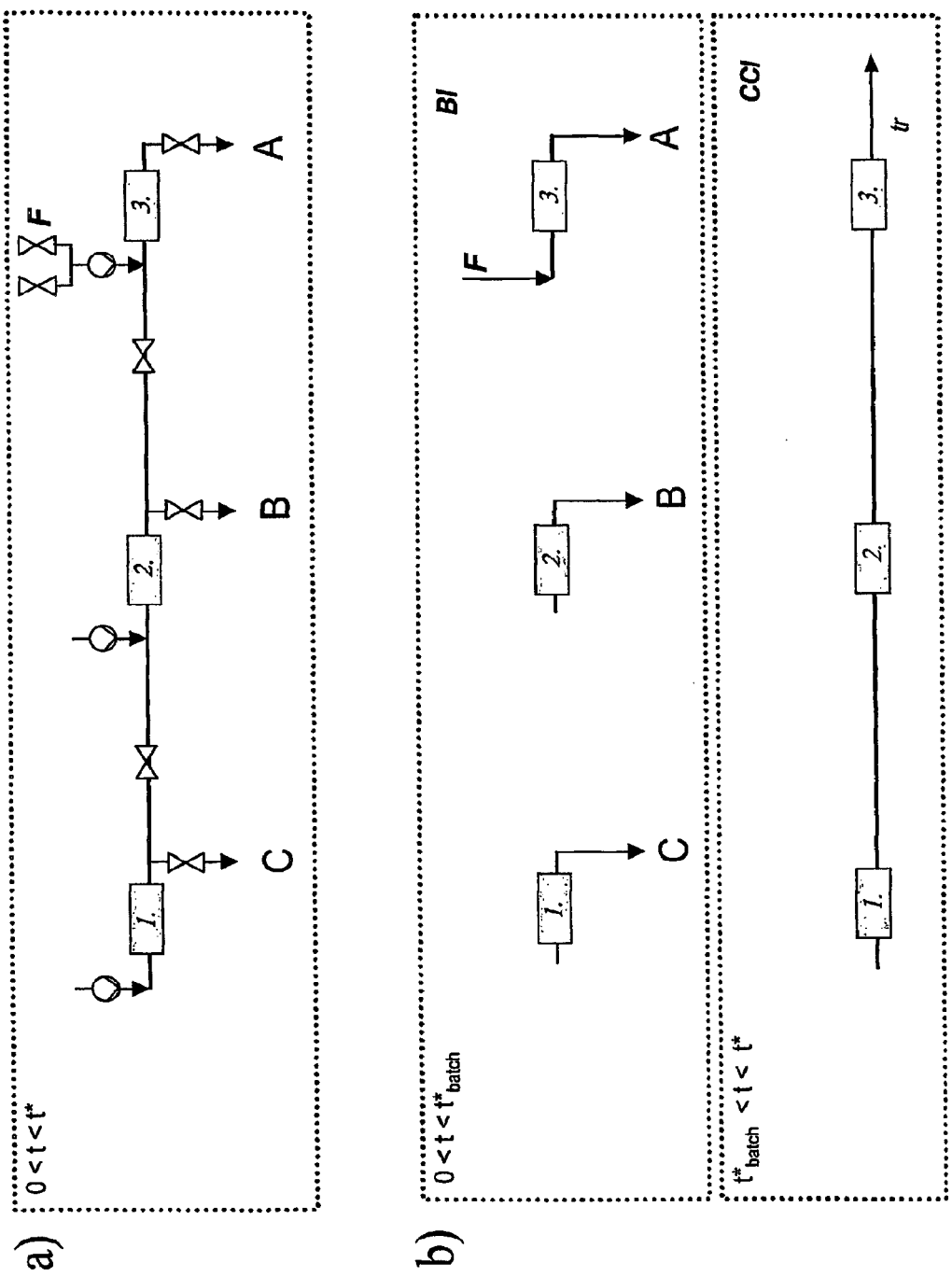
FIG. 24 shows the operation of the setup according to FIG. 20 realised explicitly with only three columns.

A general setup of the quasi- or half-continuous operation is shown in FIG. 24 a), and it can be seen that the set up is simplified dramatically, so less pumps and less connections are required. Between every column a valve changes between the two lanes, as is displayed in FIG. 24b) for the two different states.

Figure 25:
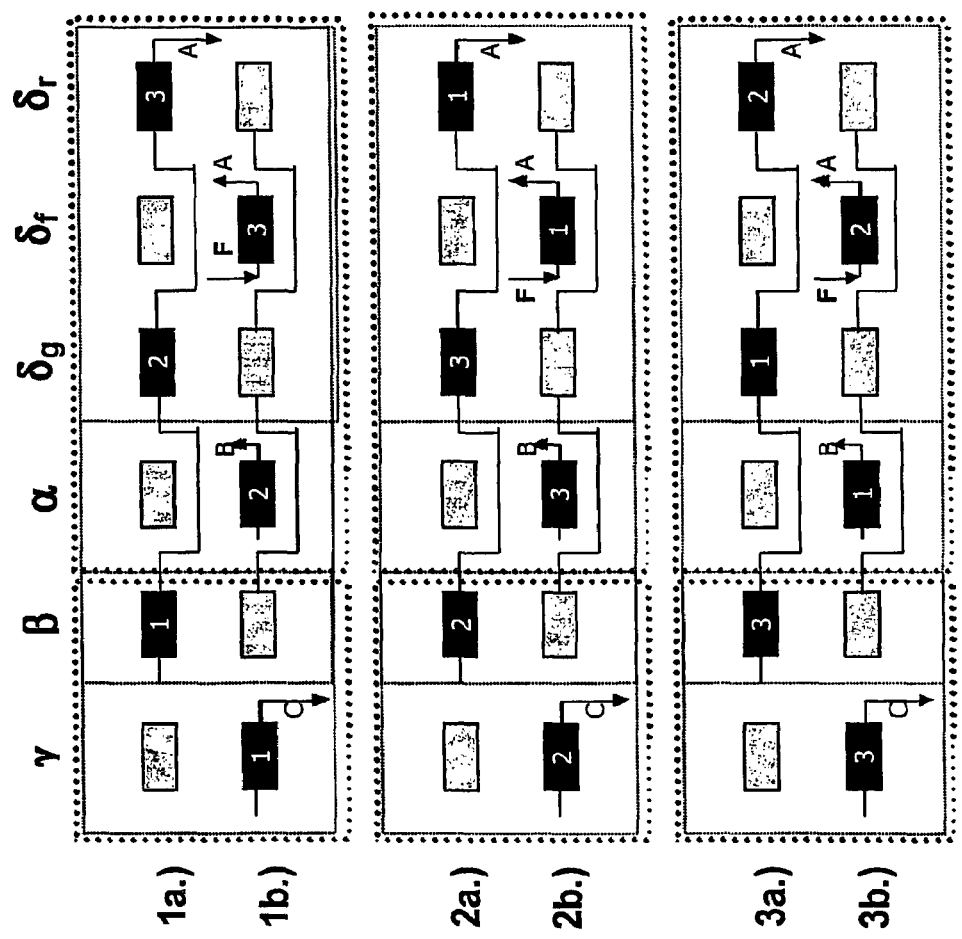
FIG. 25 shows the column positions during a cycle of the "6 Column-Unit" operated with 3 columns.

The column positions of the setup explained above are diagrammatically shown in the scheme as given in FIG. 25. A black box indicates that there is a column fulfilling the function given above, a shaded one indicates that there is no column fulfilling that function. The six different column positions are operated in the sequence 1a-1b-2a-2b-3a-3b-1a-1b-2a-2b- . . . .

Figure 26:
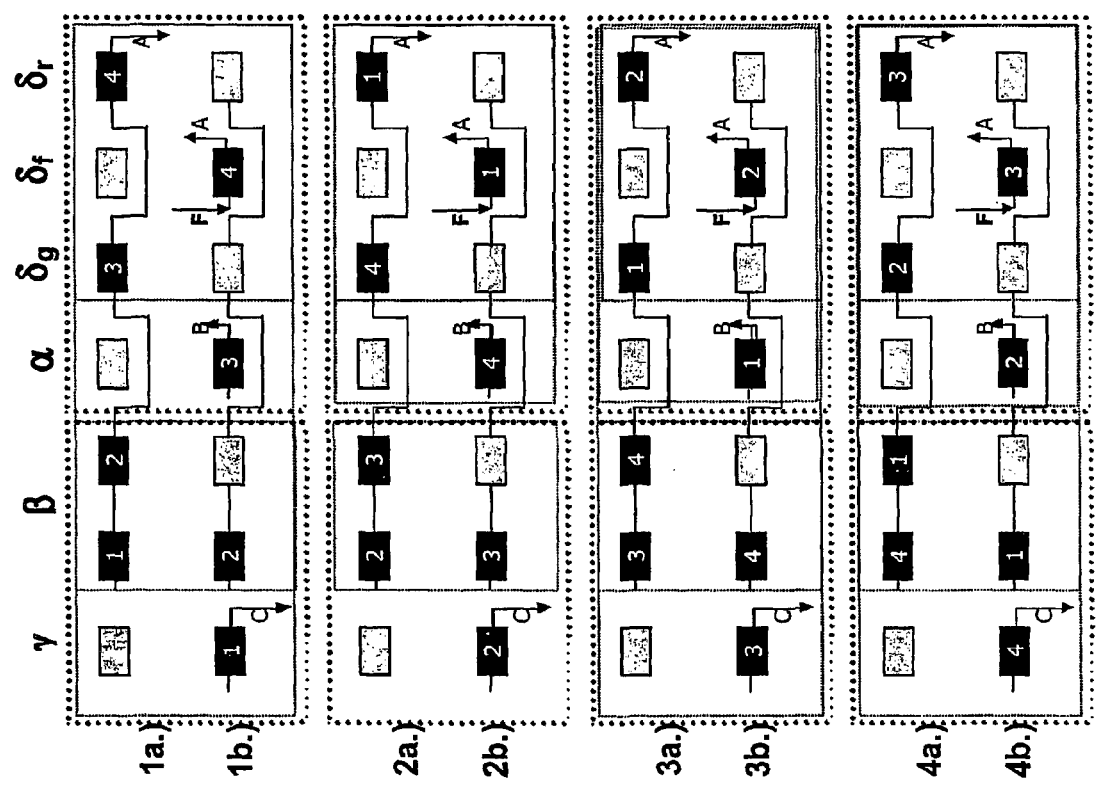
FIG. 26 shows a possible four column setup for the topology according to FIG. 21 but with two countercurrent columns in section β.

If a countercurrency inside section β and δ is required, the setup as presented in FIG. 21 but with two or more columns in section β can be transferred into semi-continuous mode. The corresponding semi-continuous setup consisting of 4 columns is shown in FIG. 26, wherein during the "β"-positions the flow rate in the first column of section β is set to zero.

In principle such a doubling of columns is possible for each of the sections and also for several sections.

Two Column Setup:

It is even possible to reduce the 3-column semi-continuous process to only 2 columns within the gist of the present invention, but then the recycling of light and heavy fractions C and A can not be fulfilled at the same time but has to be staged as well.

The principle is similar to the one for 3 columns (see above), as in three steps (steps 2.-4. in FIG. 28) only one of the three functions α, β, γ is fulfilled by a column similar to the case displayed in FIG. 19. But additionally, in this setup in one further step (step 1. in FIG. 28) none of the functions α, β, γ is fulfilled by a column but only functions of δ (step 1. in FIG. 28, functions $\delta_g$ and $\delta_r$).

Figure 27:
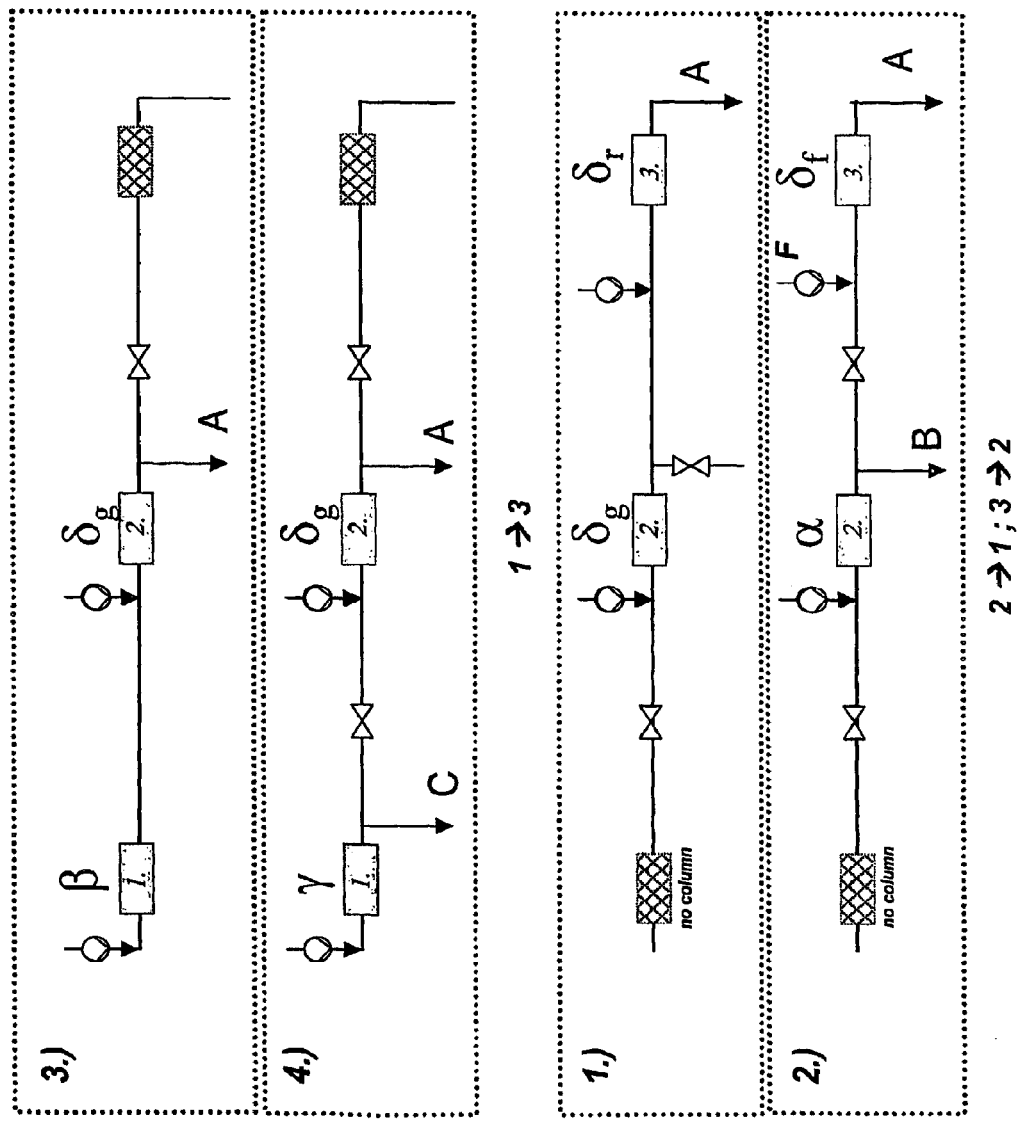
FIG. 27 shows a 2-column setup for the counter current gradient purification.

The two column setup is shown in schematically FIG. 27. The process needs to be designed in a way, so that no B leaves the column in position $\delta_g$ before the column from position γ has been switched to position $\delta_f$. Otherwise valuable product B would be lost in the light fraction outlet A.

Figure 28:
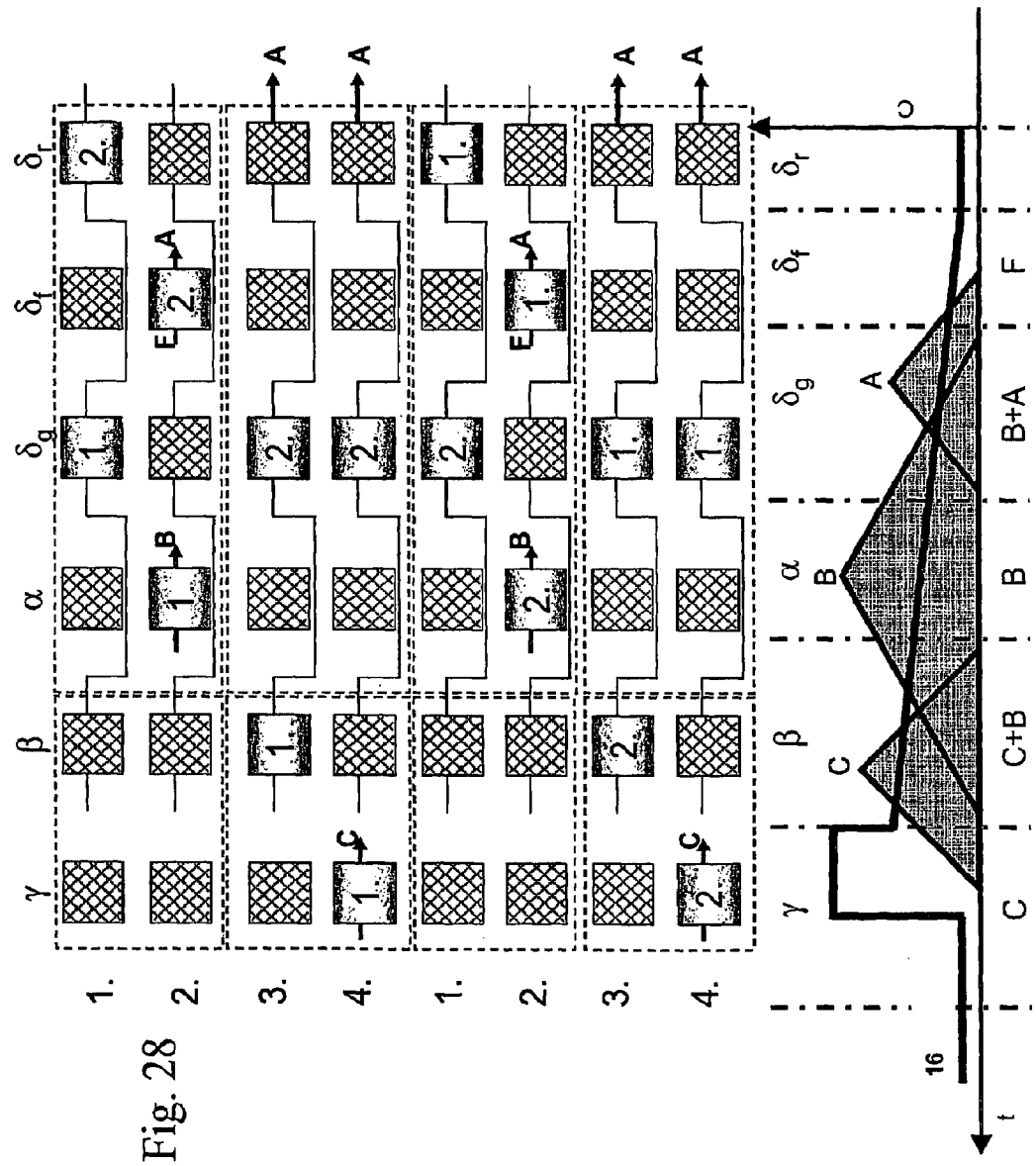
FIG. 28 shows a setup according to FIG. 27 in schematic view including the corresponding tasks of the gradient chromatogram on the bottom.

So as indicated in FIG. 27, in a first step on the top (designated with the reference numeral 3. because of the more systematic display in FIG. 28) the aim is to recycle the heavy fraction C and the intermediate fraction B between the positions β and $\delta_g$ and to collect the light fraction A (note that closed lines are indicated with a valve in between).

In the subsequent step 4. the aim is to collect the heavy fraction C and at the same time to also collect the light fraction A. This subsequent step 4. is started at the moment when only C is leaving column 1.

In these two first steps 3. and 4. the third position is not occupied by a column (hatched rectangle).

After this step 4. the column at position 1 is switched to position 3. So one can say that the upstream column in position 1. and the downstream column in position 2. interchange their places. In the two subsequent steps, position 1 will not be occupied by a column. This means that only position 2 is always occupied.

In the now following step 1. the aim is to recycle the light fraction A, and to collect tracers. This is step is carried out until pure intermediate product B starts to exit the column in position 2.

As soon as this is the case, the next step 2. is started, i.e. in this step 2. the aim is to collect the intermediate fraction B from column 2 in batch mode, at the same time to load the feed into column at position 3, and to collect very light fraction A. This step 2. is continued until just before the intermediate fraction B starts to leave the column at position 2 in a mixture together with part of the heavy fraction C.

After this step 2. the columns are switched such that the column from position 2 is moved to position 1, and the column from position 3 is moved to position 2. The process is repeated in a sequence 3-4-1-2-3-4-1-2- . . . , and it has to be noted that one full cycle includes two series of the type as given in FIG. 27.

FIG. 28 shows the same process in a more systematic display. The 2-Column Setup is given in the top part including one full cycle. In the bottom part the corresponding tasks of the gradient chromatogram for the countercurrent gradient purification is indicated. also indicated in the bottom part is the concentration profile of the modifier 16. As a matter of fact, the 2-column setup in particular works for gradient runs. The process repeats the positions: 1-2-3-4-1-2- . . . while alternating the two columns.

Sequential setup of semi-continuous units:

As already discussed above, it is also possible to combine purification units according to the invention within one plant which includes several types of purifications. The decrease to only 3 columns per purification unit as discussed above offers attractive operation modes as for example indicated below.

A general chromatographic purification process may contain several steps as for example:

Cation Exchange (CEX)

Anion Exchange (AEX)

Hydrophobic Interaction Chromatography (HIC)

Figure 29:
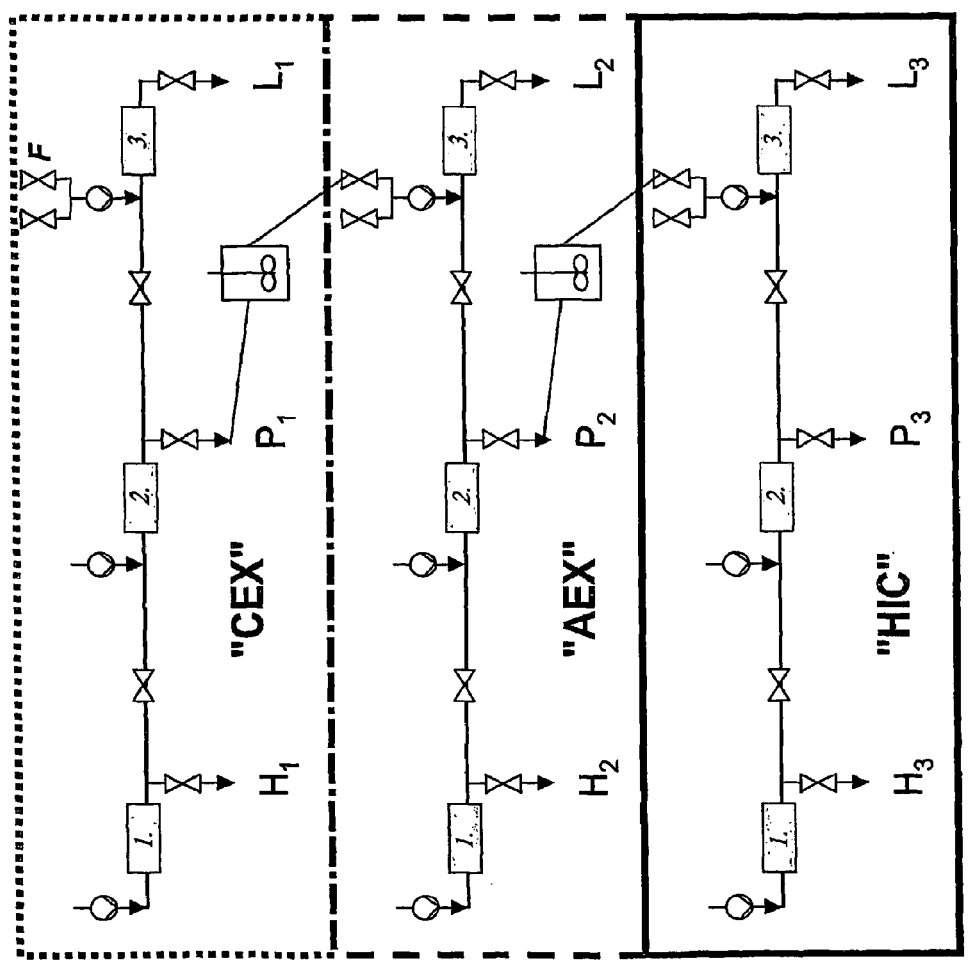
FIG. 29 shows a sequential half continuous setup with "CEX", "AEX" and "HIC" in one plant.

A sequential setup of the half-continuous purification process is suggested in FIG. 29, in which "CEX", "AEX" and "HIC" are combined in one plant.

A cleaning in place step is not considered in the FIG. 29. To enable CIP, the cheapest approach would be to have a forth position in which a column can be "parked" for cleaning in place.

Often the "AEX" step is a negative chromatographic step, where the product does not adsorb, but for example viruses do adsorb. Such a two component separation (remove virus from product) only requires 2 columns, so that position 1 in unit 2 would not be required.

The mixers between unit 1 and unit 2 and between unit 2 and unit 3 have the task to equalise the product concentrations over a cycle. In the case of nonlinear isotherms this may be an important detail.

The invention claimed is:

1. A process for continuous or quasi-continuous purification of a multi-component mixture (F) by means of individual chromatographic columns through which the mixture is fed by means of at least one solvent (s), wherein the multi-component mixture (F) at least comprises light impurities (A), an intermediate product (B) to be purified and heavy impurities (C), wherein there are two columns providing the function of at least four sections (α,β,γ,δ), in which the first section (α) is provided with at least one inlet of solvent (s) and at least one outlet for purified intermediate product (B), such that it washes the purified intermediate product (B) out of the system, but keeps the heavy impurities (C) inside the section (α), the second section (β) is provided with at least one inlet of solvent (s) and at least one outlet connected to an inlet of the fourth section (β), such that it washes the intermediate product (B), which is contaminated with heavy impurities (C) into the fourth section (δ) through said outlet, but keeps the pure heavy impurities (C) inside the section (β), the third section (γ) is provided with at least one inlet of solvent (s) and an outlet for heavy impurities (C), such that it washes out the heavy impurities (C) through said outlet and cleans the chromatographic column(s), and the fourth section (δ) is provided with at least one inlet to receive output of the outlet of the second section (β) as well as at least one inlet for feeding in the multi-component mixture (F) and at least one outlet for light impurities (A), such that it washes the light impurities (A) out of the system, but keeps the intermediate product (B) inside the section (δ), wherein after or within a switch time (t*) the last column from the first section (α) is moved to the first position of the second section (β), the last column of the second section (β) is moved to the first position of the third section (γ), the last column of the third section (γ) is moved to the first position of the fourth section (δ) and the last column of the fourth section (δ) is moved to become the first column of the first section (α), wherein the functions of the sections are either fulfilled synchronously or sequentially, wherein the fourth section (δ) comprises three sub-sections ($\delta_f$, $\delta_g$, $\delta_r$), wherein the first sub-section ($\delta_f$) comprises at least one inlet for feeding in the multicomponent mixture (F) and at least one outlet either for direct removal of light impurities (A) out of the system or into an inlet of the third sub-section ($\delta_r$), the second sub-section ($\delta_q$) comprises at least one inlet for taking up output of the second section (β) and at least one outlet connected to at least one input of the third sub-section ($\delta_r$), and the third sub-section ($\delta_r$) comprises at least one inlet for taking up output of the second sub-section ($\delta_g$) and possibly at least one inlet for taking up output of the first sub-section ($\delta_f$), and at least one outlet, and wherein:

in a first part of the switch time the two columns are connected in series for continuous elution while by means of the outlet light impurities (A) are collected, in a second part of the switch time the two columns are driven in batch mode for collecting the intermediate fraction (B) on the upstream column and light impurities (A) on the downstream column while at the same time feeding the multi-component mixture (F) into the downstream column, in a third part of the switch time the two columns are connected in series for continuous elution while by means of the outlet light impurities (A) are collected, and in a fourth part of the switch time the two columns are driven in batch mode for collecting the heavy impurities (C) on the upstream column and light impurities (A) on the downstream column, and after each switch time of the positions of the two columns are interchanged.

2. The process according to claim 1, wherein the solvent(s) fed into at least one of the sections (α,β,γ,δ) is substantially continuously varied in composition during the switch time (t*), and/or, in case of a supercritical solvent, the supercritical solvent(s) fed into at least one of the sections (α,β,γ,δ) is substantially continuously varied in density during the switch time (t*).

3. The process according to claim 1, wherein two individual columns are present, wherein groupings of the sections (α; β; γ; δ/$\delta_g$,$\beta_f$,$\delta_r$) are realized by single columns and wherein the functions of individual sections (α; β; γ; δ/$\delta_g$,$\beta_f$, δr) are fulfilled sequentially with steps of continuous or quasi-continuous elution and steps with batch elution within one switch time.

4. The process according to claim 3, wherein the solvent(s) fed into all the sections (α,β,γ,δ) is substantially continuously varied in composition with increasing or decreasing modifier concentration during the switch time (t*), and/or in case of supercritical solvent varied in density with increasing or decreasing density during the switch time (t*), and wherein along the sequence of the columns from the fourth (δ) to the first (α) section, the modifier concentration ($C_{mod}$)/density is increasing or decreasing in a way such that after a move of the columns, the modifier concentrations ($C_{mod}$)/densities in each column is substantially at the base concentration of modifier/density of the supercritical solvent at the new position of the column and such that during the following switch time (t*) the modifier concentration/density inside each column is increased or decreased to the base concentration/density of the following position after a further move of the columns.

5. The process according to claim 4, wherein the solvent(s) fed into all or some of the sections (α,β,γ,δ) is substantially continuously varied linearly or quasi-linearly or non-linearly during the switch time (t*) in composition and/or density.

6. The process according to claim 5, wherein at each solvent inlet solvent with individual constant base concentration ($C_{mod,c}$) of modifier is provided, and wherein a solvent stream with varying flow-rate and/or composition, or varying modifier concentration, ($C_{mod,v}$) is provided to several inlets and mixed with the solvent with individual constant base concentration ($C_{mod,c}$) of modifier to establish the gradient along the system.

7. The process according to claim 1, wherein at least one section (α,β,γ,δ) comprises at least two columns.

8. The process according to claim 1, wherein the second section (β) comprises at least two countercurrent sequentially connected columns.

9. The process according to claim 1, wherein pairs of sequential functions of the sections (α; β; γ; δ/$\delta_g$,$\delta_f$,$\delta_r$) are combined within one column, and wherein within one switch time steps of continuous or quasi-continuous elution and steps with batch elution, fulfilling those functions in sequential manner, alternate.

10. The process according to claim 1, wherein the feed is continuous, pulsed or with shaped concentration/density profile within one switch time (t*) and/or wherein the flows of solvents are varied within one switch time (t*) and/or wherein the switching of individual inlets/outlets is staged within one switch time (t*).

11. The process according to claim 1, wherein the flow rate in individual columns is different.

12. A method for setting up the parameters for running a process according to claim 1, wherein in a first step a gradient batch chromatogram is run, in a second step the obtained chromatogram is divided into a first part with the light fraction, a second part with the desired fraction, a third part with the desired fraction overlapping with the heavy fraction, and a fourth part with the heavy fraction only, and wherein in a third step of the parameters of the process are chosen such that the first section (α) fulfils a task equal to the gradient batch chromatogram in the time of the second part, that the second section (β) fulfils a task equal to the gradient batch chromatogram in the time of the third part, that the third section (γ) fulfils the task equal to the gradient batch chromatogram in the time of the fourth part, and that the fourth section (δ) fulfils the task equal to the gradient batch chromatogram in the time of the first part.

13. The method according to claim 12, wherein the switch time (t*) is calculated as the time until the desired fraction starts to elute with the desired purity multiplied with the flow rate ($Q_{batch}$) of the gradient batch chromatogram divided by the maximum flow rate ($Q_{max}$) of the setup and divided by the number (N) of columns in the fourth section (δ) which run that part of the gradient.

14. The method according to claim 12 or claim 13, wherein the flow rate in each column is determined based on the time the corresponding part takes in the gradient batch chromatogram multiplied with the batch flow rate ($Q_{batch}$) divided by the switch time (t*).

15. A process for continuous or quasi-continuous purification of a multi-component mixture (F) by means of individual chromatographic columns through which the mixture is fed by means of at least one solvent (s),
- wherein the multi-component mixture (F) at least comprises light impurities (A), an intermediate product (B) to be purified and heavy impurities (C),
- wherein the columns are grouped into at least four sections (α,β,γ,δ), in which
  - the first section (α) is provided with at least one inlet of solvent (s) and at least one outlet for purified intermediate product (B), such that it washes the purified intermediate product (B) out of the system, but keeps the heavy impurities (C) inside the section (α),
  - the second section (β) is provided with at least one inlet of solvent (s) and at least one outlet connected to an inlet of the fourth section (β), such that it washes the intermediate product (B), which is contaminated with heavy impurities (C) into the fourth section (δ) through said outlet, but keeps the pure heavy impurities (C) inside the section (β).
  - the third section (γ) is provided with at least one inlet of solvent (s) and an outlet for heavy impurities (C), such that it washes out the heavy impurities (C) through said outlet and cleans the chromatographic column(s), and
  - the fourth section (δ) is provided with at least one inlet to receive output of the outlet of the second section (β) as well as at least one inlet for feeding in the multi-component mixture (F) and at least one outlet for light impurities (A), such that it washes the light impurities (A) out of the system, but keeps the intermediate product (B) inside the section (δ),
- wherein after or within a switch time (t*) the last column from the first section (α) is moved to the first position of the second section (β), the last column of the second section (β) is moved to the first position of the third section (γ), the last column of the third section (γ) is moved to the first position of the fourth section (δ) and the last column of the fourth section (δ) is moved to become the first column of the first section (α),
- wherein the functions of the sections are either fulfilled synchronously or sequentially,
- wherein the system comprises three columns, wherein the functions of the first (α), the second (β) and the third (γ) section are realized by one single column, and
- wherein within one switch time
  - this single column first takes a function of the first (α) section in that it is provided with an inlet for solvent and in that its outlet is used for collecting the intermediate product (B), while the columns providing the function of the fourth (δ) section are connected in series and while by means of the outlet of the fourth (δ) section the light impurities (A) are collected,
  - subsequently this single column takes the function of the second (β) section in that it is provided with an inlet for solvent and in that its outlet is directly connected to the first column of the fourth (δ) section, while the columns providing the function of the fourth (δ) section are connected in series and while by means of the outlet of the fourth (δ) section the light impurities (A) are collected, and
  - subsequently this single column takes the function of the third (γ) section in that it is provided with an inlet for solvent and in that its outlet is used for collecting the heavy impurities (C), while the columns providing the function of the fourth (δ) section are connected in series, while by means of the outlet of the fourth (δ) section the light impurities (A) are collected and while between the columns providing the function of the fourth (δ) section the multi-component mixture (F) is fed into the fourth (δ) section.

16. The process according to claim 15, wherein the fourth section (δ) is grouped into three sub-sections ($\delta_f, \delta_g, \delta_r$), wherein
- the first sub-section ($\delta_f$) comprises at least one inlet for feeding in the multicomponent mixture (F) and at least one outlet either for direct removal of light impurities (A) out of the system or into an inlet of the third sub-section ($\delta_r$), wherein
- the second sub-section ($\delta_g$) comprises at least one inlet for taking up output of the second section (β) and at least one outlet connected to at least one input of the third sub-section ($\delta_r$), wherein
- the third sub-section ($\delta_r$) comprises at least one inlet for taking up output of the second sub-section ($\delta_g$) and possibly at least one inlet for taking up output of the first sub-section ($\delta_f$), and at least one outlet,
- wherein after or within a switch time (t*) a column from the first sub-section ($\delta_f$) is moved to the first position of the second sub-section ($\delta_g$), the last column of the second sub-section ($\delta_g$) is moved to the first position of the first section (β), the last column of the third section (γ) is moved to the first position of the third sub-section ($\delta_r$) and the last column of the third sub-section ($\delta_r$) is moved to become a column of the first sub-section ($\delta_f$),
- and wherein the functions of the sections ($\delta_f, \delta_g, \delta_r$) are either fulfilled synchronously or sequentially.

17. The process according to claim 16, wherein the first subsection ($\delta_f$) comprises at least two parallel columns, and/or wherein the second ($\delta_g$) and/or the third ($\delta_r$) sub-section comprises at least two countercurrent parallel or sequential columns.

18. The process according to claim 15, wherein the fourth section (δ) comprises three sub-sections ($\delta_f, \delta_g, \delta_r$), wherein
- the first sub-section ($\delta_f$) comprises at least one inlet for feeding in the multicomponent mixture (F) and at least one outlet either for direct removal of light impurities (A) out of the system or into an inlet of the third sub-section ($\delta_r$),
- the second sub-section ($\delta_g$) comprises at least one inlet for taking up output of the second section (β) and at least one outlet connected to at least one input of the third sub-section ($\delta_r$), and
- the third sub-section ($\delta_r$) comprises at least one inlet for taking up output of the second sub-section ($\delta_g$) and possibly at least one inlet for taking up output of the first sub-section ($\delta_f$), and at least one outlet, and wherein in the full system three columns are provided, these three columns being connected sequentially in a step (CCL) of continuous or quasi-continuous elution within a first fraction of one switch time, and being driven in a batch step (BL) for taking out individual fractions (A,B,C) of the multi-component mixture (F) within a second fraction of the switch time.

* * * * *